(12) United States Patent
Pisano et al.

(10) Patent No.: US 12,280,228 B1
(45) Date of Patent: *Apr. 22, 2025

(54) SYSTEMS AND METHODS FOR A BODILY FLUID DRAINAGE SYSTEM

(71) Applicant: Lymphatica Medtech SA, Lausanne (CH)

(72) Inventors: Marco Pisano, Préverenges (CH); Valentina Triacca, Lausanne (CH); Mathieu Aberle, Yvonand (CH); Ricardo Camilo Moreira, Lausanne (CH)

(73) Assignee: Lymphatica Medtech SA, Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/634,830

(22) Filed: Apr. 12, 2024

Related U.S. Application Data

(60) Provisional application No. 63/609,535, filed on Dec. 13, 2023.

(51) Int. Cl.
*A61M 27/00* (2006.01)
*A61L 29/08* (2006.01)
(Continued)

(52) U.S. Cl.
CPC ......... *A61M 27/002* (2013.01); *A61L 29/085* (2013.01); *A61L 29/16* (2013.01);
(Continued)

(58) Field of Classification Search
CPC ......... A61M 2202/0405; A61M 27/002; F04B 43/14
See application file for complete search history.

(56) References Cited

U.S. PATENT DOCUMENTS 3,810,259 A  5/1974 Summers
4,199,307 A * 4/1980 Jassawalla .......... F04B 43/0072
                                                  417/474
(Continued)

FOREIGN PATENT DOCUMENTS

CN  203694372 U  7/2014
DE  202009011664 U1  12/2009
(Continued)

OTHER PUBLICATIONS

Luo et al., "Soft kink valves," Journal of the Mechanics and Physics of Solids, 131:230-239 (Jul. 2019) (Year: 2019).*

(Continued)

*Primary Examiner* — Sarah Al Hashimi
*Assistant Examiner* — Arjuna P Chatrathi
(74) *Attorney, Agent, or Firm* — Greenberg Traurig, LLP; Christopher C. Bolten; Robert D. Ward

(57) ABSTRACT

Systems and methods are provided for a bodily fluid management system for pumping bodily fluid such as lymph. The bodily fluid management system may include an implantable pump with a rotor having a magnetic portion and inlet and outlet tubes that connect to a fluid chamber. The fluid chamber has a volume that can be selectively reduced or increased via the rotor. The rotor is designed to periodically open and close kinking valves at each of the inlet and outlet tube to permit bodily fluid to enter the fluid chamber during an intake cycle and exit the fluid chamber during a discharge cycle. The magnetic portion of the rotor may be caused to rotate by an external controller that is positioned outside of the body and adjacent to the pump. The external controller may have a magnet that magnetically interfaces with the rotor to cause the rotor to rotate.

30 Claims, 20 Drawing Sheets

(51) Int. Cl.
*A61L 29/16* (2006.01)
*A61L 33/00* (2006.01)
*A61M 25/00* (2006.01)

(52) U.S. Cl.
CPC ........ *A61L 33/0011* (2013.01); *A61M 25/003* (2013.01); *A61M 25/0045* (2013.01); *A61L 2300/236* (2013.01); *A61L 2300/42* (2013.01); *A61M 2025/0046* (2013.01); *A61M 2202/0405* (2013.01); *A61M 2205/103* (2013.01)

(56) References Cited

U.S. PATENT DOCUMENTS

| | | | |
|---|---|---|---|
| 4,240,434 | A | 12/1980 | Newkirk |
| 4,443,214 | A | 4/1984 | Marion |
| 4,610,658 | A | 9/1986 | Buchwald et al. |
| 4,657,530 | A | 4/1987 | Buchwald et al. |
| 4,725,207 | A | 2/1988 | Buchwald et al. |
| 4,850,955 | A | 7/1989 | Newkirk |
| 5,165,873 | A * | 11/1992 | Meijer ............... A61M 5/14228 417/474 |
| 5,762,599 | A | 6/1998 | Sohn |
| 5,810,760 | A | 9/1998 | Andrews |
| 5,964,583 | A * | 10/1999 | Danby ................. F04B 43/082 417/474 |
| 6,190,347 | B1 | 2/2001 | Kensey |
| 6,749,580 | B2 | 6/2004 | Work et al. |
| 7,059,840 | B2 * | 6/2006 | Corwin ................ F04B 43/082 417/474 |
| 7,491,163 | B2 | 2/2009 | Viole et al. |
| 7,901,419 | B2 | 3/2011 | Bachmann et al. |
| 8,157,792 | B2 | 4/2012 | Dolliver et al. |
| 8,398,577 | B2 | 3/2013 | Burnett |
| 8,517,973 | B2 | 8/2013 | Burnett |
| 9,039,652 | B2 | 5/2015 | Degen et al. |
| 9,144,660 | B2 | 9/2015 | Degen |
| 9,421,348 | B2 | 8/2016 | Lenihan et al. |
| 9,474,883 | B2 | 10/2016 | Cornet et al. |
| 9,913,968 | B2 | 3/2018 | Burnett |
| 10,603,214 | B2 | 3/2020 | Bigler et al. |
| 10,765,844 | B2 | 9/2020 | Pisano et al. |
| 10,864,363 | B2 | 12/2020 | Hakim |
| 2004/0098113 | A1 * | 5/2004 | Forsell ................. A61M 60/515 623/1.25 |
| 2004/0147871 | A1 | 7/2004 | Burnett |
| 2004/0230179 | A1 | 11/2004 | Shehada |
| 2004/0249360 | A1 | 12/2004 | Spehalski |
| 2005/0069436 | A1 | 3/2005 | Shibasaki |
| 2005/0277804 | A1 | 12/2005 | Pecor |
| 2005/0277865 | A1 | 12/2005 | Gharib et al. |
| 2009/0099498 | A1 | 4/2009 | Demers et al. |
| 2012/0245543 | A1 | 9/2012 | Herbert |
| 2012/0277657 | A1 | 11/2012 | Kroeter et al. |
| 2014/0114227 | A1 | 4/2014 | Zamarripa et al. |
| 2014/0207043 | A1 | 7/2014 | Anand et al. |
| 2015/0305746 | A1 | 10/2015 | Johnson et al. |
| 2015/0343186 | A1 * | 12/2015 | Nitzan ................ A61M 1/3659 604/9 |
| 2016/0030663 | A1 | 2/2016 | Adaniya et al. |
| 2017/0197066 | A1 * | 7/2017 | Itkin ..................... A61M 39/24 |
| 2017/0304597 | A1 | 10/2017 | Forsell |
| 2018/0229015 | A1 * | 8/2018 | Pisano ................ A61M 27/002 |
| 2018/0339102 | A1 * | 11/2018 | Barraud ................ F04B 19/006 |
| 2020/0197675 | A1 * | 6/2020 | Pisano ..................... A01K 9/00 |
| 2020/0282200 | A1 | 9/2020 | Hakim et al. |
| 2020/0353231 | A1 | 11/2020 | Sharon et al. |
| 2020/0362858 | A1 * | 11/2020 | Shepherd ................ F04B 43/14 |
| 2021/0069409 | A1 | 3/2021 | Castleberry et al. |
| 2021/0244381 | A1 | 8/2021 | Sweeney et al. |
| 2021/0298649 | A1 | 9/2021 | Essalik et al. |
| 2022/0143277 | A1 | 5/2022 | Cheng |
| 2022/0241554 | A1 * | 8/2022 | Conia ................ A61M 25/0017 |
| 2023/0055098 | A1 * | 2/2023 | Fech ...................... A61M 5/30 |

FOREIGN PATENT DOCUMENTS

| | | |
|---|---|---|
| EP | 0066685 A1 | 12/1982 |
| EP | 0270205 A2 | 6/1988 |
| EP | 0617596 A1 | 10/1994 |
| EP | 1327460 A2 | 7/2003 |
| EP | 3634563 B1 | 3/2021 |
| FR | 2710269 A1 | 3/1995 |
| GB | 2350794 A | 12/2000 |
| WO | WO-9000911 A1 | 2/1990 |
| WO | WO-9115254 A1 | 10/1991 |
| WO | WO-2005115502 A2 | 12/2005 |
| WO | WO-2009096852 A1 | 8/2009 |
| WO | WO-2012106693 A2 | 8/2012 |
| WO | WO-2012142473 A1 | 10/2012 |
| WO | WO-2014062679 A1 | 4/2014 |
| WO | WO-2014078431 A1 | 5/2014 |
| WO | WO-2015186005 A2 | 12/2015 |
| WO | WO-2015200797 A2 | 12/2015 |
| WO | WO-2016055896 A1 | 4/2016 |
| WO | WO-2018037359 A1 | 3/2018 |
| WO | WO-2021146589 A1 | 7/2021 |
| WO | WO-2021226486 A1 | 11/2021 |
| WO | WO-2022178523 A1 | 8/2022 |

OTHER PUBLICATIONS

Ainla A., "The Multifunctional Pipette: a Microfluidic Technology For the Biosciences," Chalmers University of Technology, 2013, Table 2.1, p. 12.

Boosting brain's waste removal system could improve Alzheimer's outcomes, May 4, 2021, available at https://www.nih.gov/news-events/nih-research-matters/boosting-brains-waste-removal-system-could-improve-alzheimers-outcomes.

Deo S.V., et al., "Prevalence And Risk Factors For Development of Lymphedema Following Breast Cancer Treatment," Indian Journal of Cancer, 2004, vol. 41, No. 1, p. 8.

Ding et al., "Impaired meningeal lymphatic drainage in patients with idiopathic Parkinson's disease," Nature Medicine 27(3):1-8, (Mar. 2021) DOI:10.1038/s41591-020-01198-1, available at https://www.researchgate.net/publication/348588639_Impaired_meningeal_lymphatic_drainage_in_patients_with_idiopathic_Parkinson's_disease.

International Search Report and Written Opinion for International Application No. PCT/EP2018/063994, mailed Aug. 21, 2018, 10 Pages.

International Search Report and Written Opinion for International Application No. PCT/IB2015/057394, mailed Jan. 19, 2016, 13 Pages.

Jessen et al., "The Glymphatic System: a Beginner's Guide." Neurochem Res., 40(12):2583-2599 (Dec. 2015).

Kissell L., H.R. 4662—Lymphedema Diagnosis and Treatment Cost Saving Act of 2010, 111th Congress, 2nd Session, Feb. 23, 2010.

Liu et al., "The cervical lymph node contributes to peripheral inflammation related to Parkinson's disease," J Neuroinflammation 20:93 (2023). https://doi.org/10.1186/s12974-023-02770-5.

Luo et al., "Soft kink valves," Journal of the Mechanics and Physics of Solids, 131:230-239 (Jul. 2019).

Ma et al., "Outflow of cerebrospinal fluid is predominantly through lymphatic vessels and is reduced in aged mice," Nat Commun 8, 1434 (Nov. 2017). https://doi.org/10.1038/s41467-017-01484-6 https://www.nature.com/articles/s41467-017-01484-6#citeas.

Moffatt, et al., "Lymphoedema: an Underestimated Health Problem," QJM, 96(10):731-738 (Oct. 2003).

Olszewski et al., "Edema Fluid Can Be Successfully Evacuated from the Lymphedematous Limbs by Implantation of Silicone Tubing Bypassing the Site of Flow Obstruction Long-Term Observations," Lymphatic Research and Biology, pp. 1-8 (Feb. 2019).

Triacca et al., "Experimental Drainage Device to Reduce Lymphoedema in a Rat Model," Eur J Vasc Endovasc Surg, 57:859-867 (May 2019).

* cited by examiner

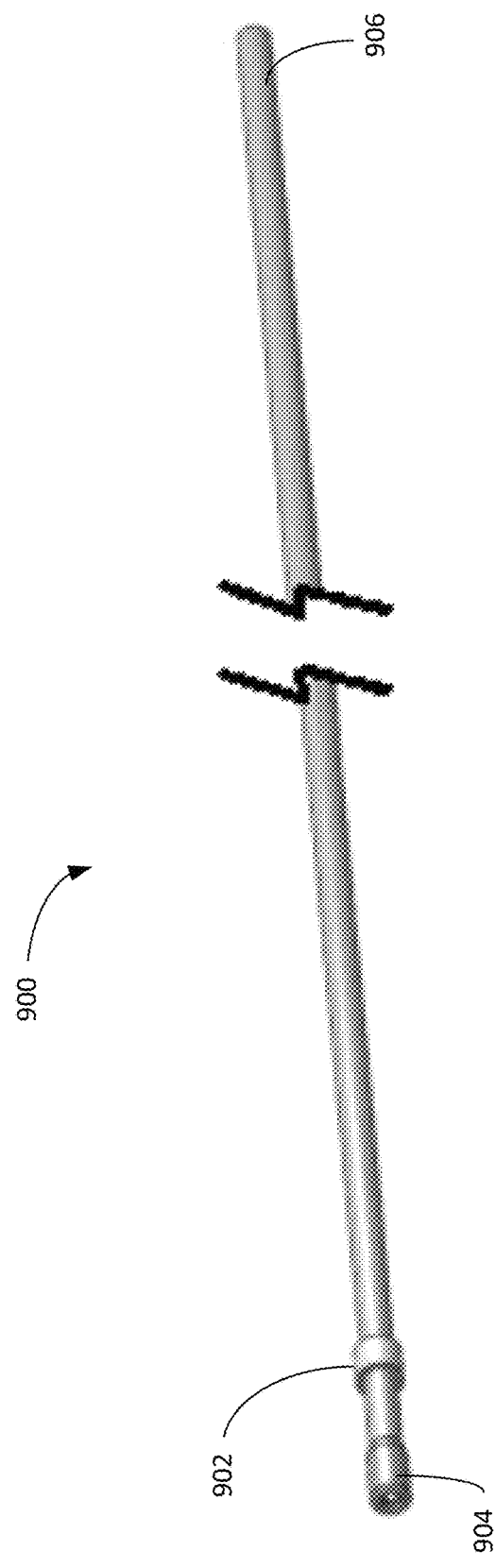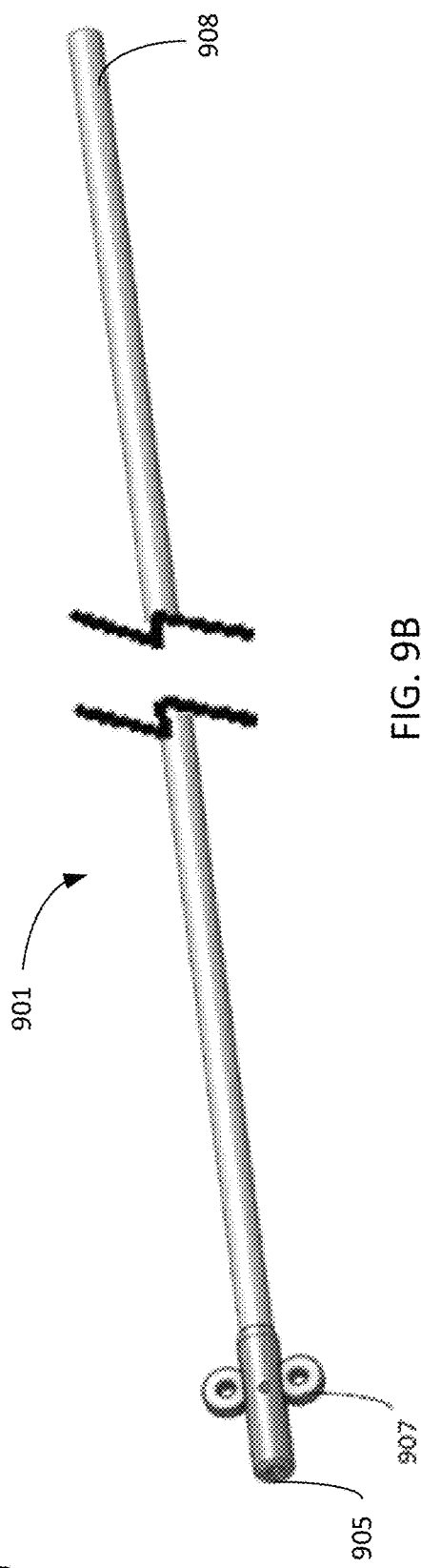
FIG. 9A
FIG. 9B
AMENDED

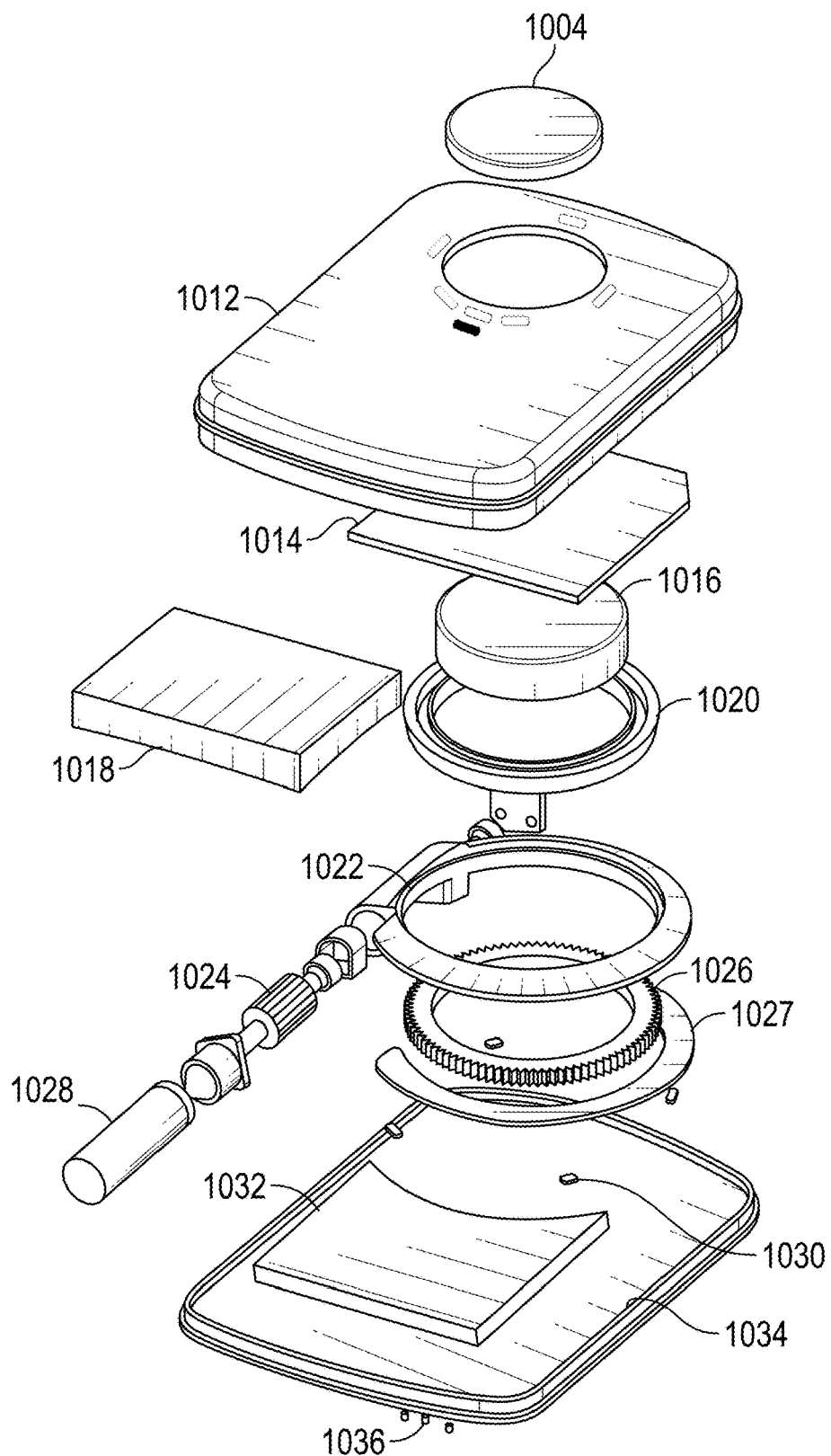
FIG. 10B
AMENDED

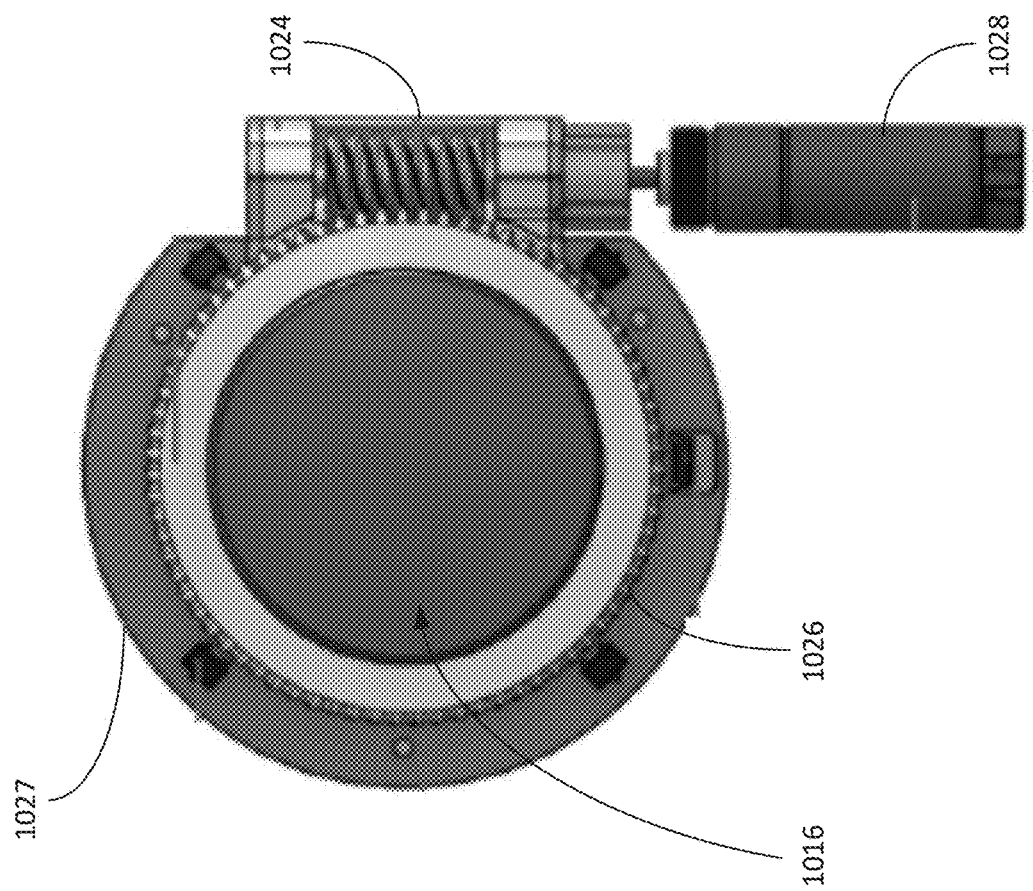
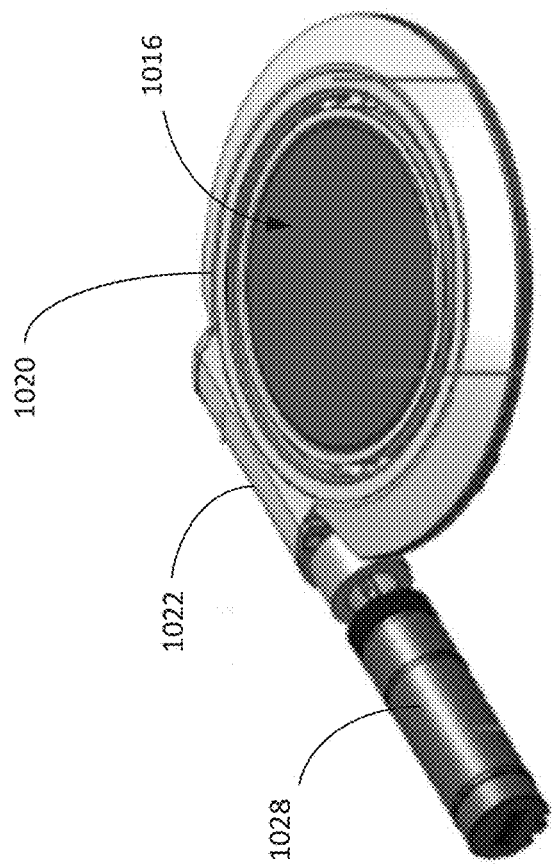
FIG. 10D
FIG. 10C

SYSTEMS AND METHODS FOR A BODILY FLUID DRAINAGE SYSTEM

CROSS-REFERENCE TO RELATED APPLICATIONS

This application claims priority to U.S. Provisional Patent Appl. No. 63/609,535, filed Dec. 13, 2023, the entire contents of which are incorporated herein by reference.

TECHNICAL FIELD

This technology relates, in general, to bodily fluid drainage, for example, a lymphatic drainage system including an implantable pump for moving lymph in a patient.

BACKGROUND

The lymphatic system is made of a network of lymph vessels, tissues, and organs, that carry lymphatic fluid through the body. Buildup of lymphatic fluid (also known as lymph) under the skin, called lymphedema, is often the result of chronic disease or a side effect of medical treatment such as certain cancer treatments (e.g., radiation). It is estimated that about 10 million individuals across the United States and Europe suffer from lymphedema.

When the lymphatic system is no longer able to properly distribute the lymph throughout the body, either due to disease or medical treatment, such fluid may start to build up and cause a limb such as an individual's arm or leg to swell. The resulting swelling caused by a buildup of lymph is known to result in significant pain and recurrent infections. To date, there is no existing cure to lymphedema.

While there is no cure to lymphedema, various therapies and treatments have been developed. For example, manual lymphatic drainage via massaging is commonly used to urge and/or facilitate lymph drainage. Compression therapy may also be used, for example by applying an elastic or compressive wrap to the swollen limb. While manual lymphatic drainage may help temporarily alleviate symptoms, it is time consuming and only offers limited and temporary relief. Further compression therapy requires strict patient compliance, is time consuming and restricts activity.

In addition to complications above relating to lymphedema, lymph flow is known to have implications with respect to neurodegenerative diseases such as Parkinson's and Alzheimer's disease. For example, fluid buildup due to meningeal lymphatic dysfunction could have undesirable effects beyond those listed above with respect to lymphedema.

Accordingly, there is a need for improved methods and systems for lymph management for redistributing lymph build up to alleviate symptoms of lymphedema and other related symptoms and effects.

SUMMARY

Provided herein are systems and methods for bodily fluid management using an implantable pump. For example, the implantable pump may be connected to implanted catheters for moving fluid from one location in the body to another. The implantable pump may be externally driven by an external controller that is exterior to the patient and positioned in proximity to the implantable pump such that a magnetic portion of the external controller magnetically interfaces with a magnetic portion of the implantable pump. The implantable pump may include one or more kinking valves to selectively move fluid from an inlet catheter to an outlet catheter. Using the implantable pump, fluid may be drained from an edematous area to interstitial space in a discharge region.

A lymphatic drainage system for lymphatic fluid management in a patient is provided herein. The lymphatic drainage system may include a housing designed to be implanted within the patient, an inlet tube positioned within the housing, the inlet tube designed to be in fluid communication with a first bodily portion to receive bodily fluid, an outlet tube positioned within the housing, the outlet tube designed to be in fluid communication with a second bodily portion, a fluid chamber positioned within the housing and designed to be in fluid communication with the inlet tube and the outlet tube, a rotor positioned within the housing and designed to rotate to change a volume of the fluid chamber, and a lever in mechanical communication with the rotor and designed to move between an open position and a closed position responsive to rotation of the rotor to cause the inlet tube to periodically kink such that the bodily fluid is pumped from the first bodily portion towards the second bodily portion via the inlet tube, the fluid chamber, and the outlet tube.

The first bodily portion may be in fluid communication with the patient's lymphatic system such that the bodily fluid pumped by the implantable pump includes lymphatic fluid. The rotor may include a first magnetic portion, the lymphatic drainage system may further include an external controller including a second magnetic portion and a motor designed to cause the second magnetic portion to move to induce movement in the first magnetic portion, thereby causing the rotor to rotate. The inlet tube may be designed to form a U-shape when the lever is in the closed position. The fluid flow in the inlet tube may be entirely obstructed when the inlet tube is kinked by the lever. The lever may cause the inlet tube to kink as the rotor rotates to reduce the volume of the fluid chamber. The rotor may be rotatably coupled to the housing at an eccentric position of the rotor.

The implantable pump may further include a cam in mechanical communication with the rotator and designed to interface with a cam receiving portion of the lever to cause the lever to move between the open position and the closed position as the rotor rotates. The implantable pump further including a biasing portion designed to interface with the cam to bias the lever to transition to the closed position. The implantable pump further including a second lever in mechanical communication with the rotor and designed to move between a second open position and a second closed position responsive to rotation of the rotor to cause the outlet tube to periodically kink. The implantable pump may further include a piston designed to interface with the rotor such that rotation of the rotor causes the piston to increase and decrease the volume of the fluid chamber.

An elastic membrane may be positioned between the piston and the fluid chamber such that the piston does not contact the lymphatic fluid in the fluid chamber. The fluid chamber may include a rigid shell and an internal membrane connected to the elastic membrane such that fluid that enters the fluid chamber is contained between the internal membrane and the elastic membrane. The lymphatic drainage system may further include an inlet connector and an outlet of the inlet tube may be coupled to the fluid chamber. An inlet of the inlet tube may be coupled to the inlet connector, the inlet connector including at least one protrusion designed to couple to an inlet catheter designed for delivering lymphatic fluid to the implantable pump. The lymphatic drainage system may further include an inlet catheter coupled to the inlet tube, the inlet catheter including a first lumen, a second lumen, a first plurality of openings positioned at a first end region of the inlet catheter, and a second plurality of openings positioned between the first end region and a second end region of the inlet catheter, the first plurality of openings in fluid communication with the first lumen and the second plurality of openings in fluid communication with the second lumen. The inlet catheter may include a main lumen in fluid communication with at least the first lumen and the second lumen. The lymphatic drainage system may further include an outlet catheter coupled to the outlet tube at a first end of the outlet catheter, the outlet catheter including a second end designed to be positioned in an interstitial space of the patient. The external controller may further include includes a worm-gear and the motor may be designed to turn the worm-gear to cause the second magnetic portion to rotate.

A method for pumping lymphatic fluid in a patient is provided herein. The method may include implanting an implantable pump including a housing, an inlet tube, a fluid chamber, an outlet tube, and a rotor, causing the rotor to transition between an intake position and a discharge position to change a volume of the fluid chamber and to cause the inlet tube and the outlet tube to periodically kink responsive to rotation of the rotor, wherein the implantable pump is designed to cause lymphatic fluid to enter the fluid chamber via the inlet tube when the rotor is in the intake position and to cause the lymphatic fluid to exit the fluid chamber via the outlet tube when the rotor is in the discharge position to thereby pump the lymphatic fluid from a first bodily portion towards a second bodily portion. The rotor may be rotatably coupled to the housing at an eccentric position on the rotor. Causing the rotor to transition may include causing the rotor to transition responsive to an external magnet worn by the patient. Implanting the implantable pump may include implanting the implantable pump in the patient's arm to drain the lymphatic fluid from an edematous area of the patient's arm to a supra-clavicular area of the patient. Implanting the implantable pump may include implanting the implantable pump in the patient's leg to drain the lymphatic fluid from an edematous area of the patient's leg to a subcutaneous space in the abdominal or dorsal area of the patient. Implanting the implantable pump may include implanting the implantable pump in the patient's upper body to drain the lymphatic fluid from brain lymphatics to axillary lymph nodes of the patient.

Yet another lymphatic drainage system for lymphatic fluid management in a patient is provided herein. The lymphatic drainage system may include an implantable pump including a housing designed to be implanted within the patient an inlet tube designed to be in fluid communication with a first bodily portion to receive bodily fluid, an outlet tube designed to be in fluid communication with a second bodily portion, a fluid chamber positioned within the housing and designed to be in fluid communication with the inlet tube and the outlet tube, a rotor positioned within the housing and designed to rotate to change a volume of the fluid chamber, and a membrane defining a wall of the fluid chamber, the membrane designed to stretch responsive to rotation of the rotor to reduce the volume of the fluid chamber towards the closed position such that the bodily fluid is pumped from the first bodily portion towards the second bodily portion via the inlet tube, the fluid chamber, and the outlet tube.

The lymphatic drainage system may further include a second membrane defining a second wall of the fluid chamber, wherein the second membrane does not change shape responsive to rotation of the rotor, and wherein the first membrane and the second membrane are hermetically sealed to form a fluid chamber. The lymphatic drainage system may further include an inlet catheter in fluid communication with the first bodily portion and the inlet tube and an outlet catheter in fluid communication with the second bodily portion and the outlet tube. The inlet tube, the inlet catheter, the outlet tube, the outlet catheter, the first membrane, and the second membrane may be all made of identical material. The identical material may include a silicone elastomer coated with covalent heparin, and the bodily fluid may only contact the identical material when using the implantable pump. An end of the membrane may be fixed within the housing and a portion of the membrane covering a piston that interfaces with the rotor may stretch responsive to rotation of the rotor.

A method for increasing lymphatic flow from a brain using a lymphatic drainage system is provided herein. The method may include providing a pump having an inlet tube in fluid communication with a cervical, occipital, and/or posterior auricular area and an outlet tube in fluid communication with another body area, activating the pump to locally decrease interstitial pressure in the cervical, occipital, and/or posterior auricular area where lymph nodes and lymphatic vessels are located to increase lymphatic flow from the brain via the inlet tube and the outlet tube. The method may further include activating the pump to increase lymphatic flow from the brain to treat a neurodegenerative disease. The method may further include implanting the pump.

An outlet of the outlet tube may be in fluid communication with a lymphatic duct such as a thoracic or right lymphatic duct or a lymphatic trunk or is placed subcutaneously in a subclavian area. An outlet of the outlet tube may be in fluid communication with a subclavian lymphatic trunk. An inlet of the inlet tube may be cannulated in a lymphatic in the cervical area or an accessible higher lymphatic vessel and may be designed to increase a flow rate from a cervical lymphatic vessel. The lymphatic may be an upper left or right jugular lymphatic trunk. An inlet of the inlet tube may be placed subcutaneously in the cervical area and may be designed to absorb free fluid from tissue in the cervical area and to increase a flow rate in the cervical region. The pump may include a kinking valve designed to increase the lymphatic flow.

A catheter for use in a lymphatic drainage system is provided herein. The catheter may include an elongated shaft having an inlet region configured to be implanted in a patient to drain fluid that collects in a subcutaneous interstitial space, the elongated shaft further including an outlet region designed to be coupled to an implantable pump, the elongated shaft including a first lumen, a second lumen, a main lumen in fluid communication with at least the first lumen and the second lumen, a first plurality of openings positioned at a first end region of the elongated shaft, and a second plurality of openings positioned between the first end region and a second end region of the elongated shaft, the first plurality of openings in fluid communication with the first lumen and the second plurality of openings in fluid communication with the second lumen.

The catheter may further include a third lumen in fluid communication with the main lumen, the catheter further including a third plurality of openings positioned between the second plurality of openings and the second end region of the elongated shaft, the third plurality of openings in fluid communication with the third lumen. The catheter may further include a fourth lumen in fluid communication with the main lumen, the catheter further including a fourth plurality of openings positioned between the third plurality of openings and the second end region of the elongated shaft, the fourth plurality of openings in fluid communication with the fourth lumen. The first plurality of openings may be circumferentially offset along the elongated shaft from the second plurality of openings.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

FIGS. 9A-9B illustrate perspective views of outlet catheters including anchoring portions respective outlets of the outlet catheters.

FIGS. 10A-10D illustrate perspective and exploded views of the external controller used together with the implantable pump to pump bodily fluid.

FIG. 16 schematically illustrates an example architecture of an external controller of the bodily fluid drainage system, in accordance with one or more embodiments of the disclosure.

The foregoing and other features of the present invention will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

This technology relates to a bodily fluid drainage system such a lymphatic fluid (i.e., lymph) drainage system including an implantable pump, which may include one or more kinking valves. The implantable pump may include a rotor having a magnetic portion that may be caused to rotate by an external controller having a magnetic portion and a motor to rotate the magnetic portion on the external controller. The implantable pump may be connected to inlet and outlet catheters and may include kinking valves for selectively directing fluid received from an inlet catheter to an outlet catheter. The inlet catheter may be positioned in an edematous area and the outlet catheter may be positioned in an interstitial space of a discharge region. For example, the implantable pump may be positioned in the patient's leg, arm, or neck area to alleviate lymph build-up in the patient (e.g., the user). In one example, the inlet region be implanted in a patient to drain fluid (e.g., lymph) that collects in a subcutaneous interstitial space of the patient.

Figure 1A:
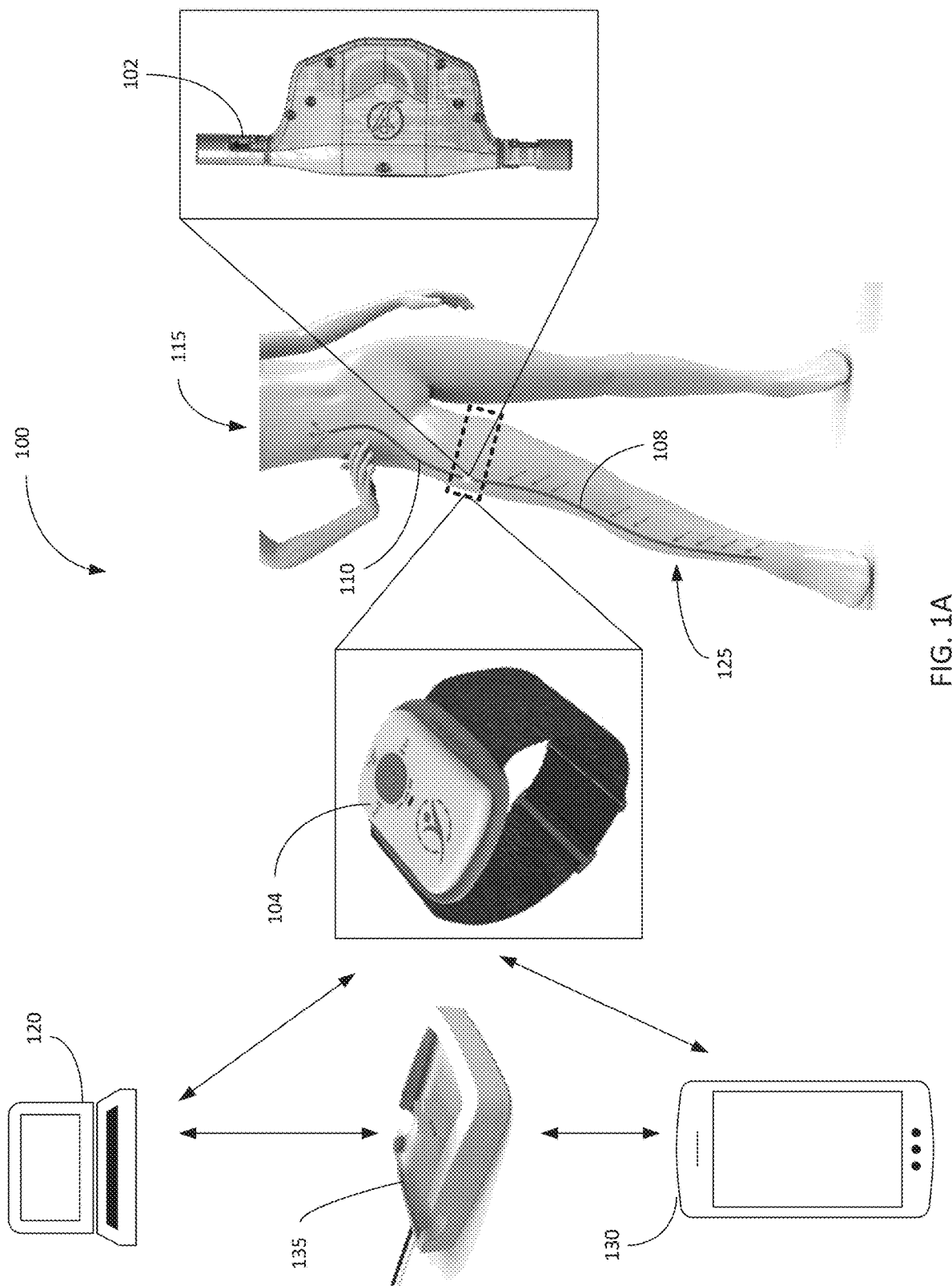
FIG. 1A illustrates an exemplary bodily fluid drainage system including an implantable pump implanted in a leg of a patient for managing bodily fluid in a patient.
Figure 1B:
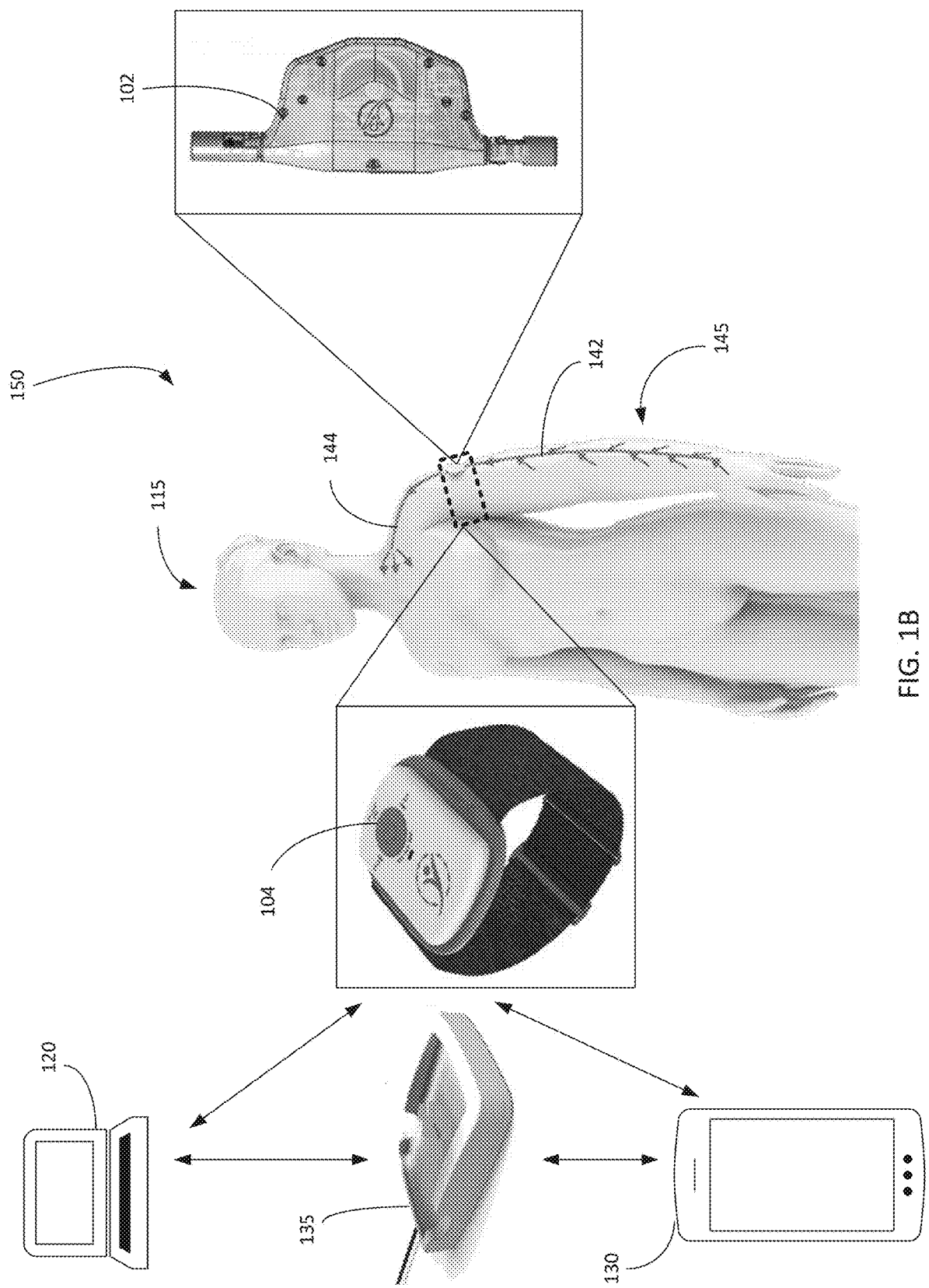
FIG. 1B illustrates an exemplary bodily fluid drainage system including an implantable pump implanted in an arm of a patient for managing bodily fluid in a patient.

Referring now to FIGS. 1A-1B, exemplary bodily fluid drainage systems including an implantable pump implanted in a leg or arm of a patient for managing bodily fluid in the patient are illustrated. As shown in FIG. 1A, implantable pump 102 of bodily fluid drainage system 100 may be implanted in leg 125 of patient 115. Leg 125 of patient 115 may have lymph buildup and patient 115 may have lymphedema.

Implantable pump 102 may be connected to inlet catheter 108 and outlet catheter 110. Inlet catheter 108 and outlet catheter 110 may each be implanted in patient 115. Inlet catheter 108 may have multiple lumens and may extend along a portion of leg 125. Outlet catheter 110 may extend from implantable pump 102 to the abdomen or dorsal area of patient 115 for example. On one example, inlet catheter 108 may be positioned in an edematous area the leg 125 and outlet catheter may be positioned in an interstitial space of a discharge region in the abdomen or dorsal area of patient 115.

Implantable pump 102 may include a rotor with a magnetic portion that rotates to cause a piston to move to change a volume of the fluid chamber to create a negative pressure to cause lymph to enter inlet catheter 108 and enter the fluid chamber and subsequently may cause the piston to force the lymph out of the fluid chamber and into the outlet catheter ultimately to be discharged into the discharge area at the outlet of the outlet catheter. In this manner, lymph that has built up in leg 125 may be redirected to the discharge area in the abdomen or dorsal area of the patient, thereby reducing swelling in leg 125.

External controller 104 may be positioned adjacent to or otherwise near implantable pump 102. For example, external controller 104 may include an elastic and/or adjustable band that may secure external controller 104 in proximity to implantable pump 102 such that a magnetic portion in external controller 104 may magnetically interface with the magnetic portion of the rotor of implantable pump 102 via a magnetic field. Controller 104 may include hall effect sensors for determining alignment with the implantable pump and/or lights or other visual indicators for indicating proper alignment or misalignment to the user.

External controller 104 may include input buttons, visual indicators, audio indicators, a motor and a magnetic portion for magnetically interfacing with a magnetic portion of implantable pump 102. External controller 104 may further include a processor (e.g., microprocessor) which may control operation of the buttons, visual indicators, audio indicators, motor, and communication with other devices. The processor may be any suitable processor executing the operations and tasks described with respect to the implantable pump described herein.

External controller 104 may be worn for a certain period of time by the patient (e.g., 1-2 hours a day, 5 hours a day, 10 hours a day, or 24 hours a day). The external controller may be used to set operational parameters for implantable pump 102, set to achieve a certain drainage velocity and/or lymph flow rate (e.g., mL/min) desired for the patient, a certain run time, a suggested therapy time per day, and/or communicate certain messages or information to the patient. The rotor of implantable pump 102 may rotate at a rate of or between 1 and 20 rotations per minute (RPM) or any other suitable rate. Implantable pump 102 may pump fluid (e.g., lymph) at a rate of or between 0.1 and 2 mL/min or any other suitable rate.

External controller 104 may communicate, via any suitable wired or wireless system (e.g., Wi-Fi, cellular network, Bluetooth, Bluetooth Low Energy (BLE), near field communication protocol, etc.) with one or more devices. For example, external controller 104 may communicate with computing device 120, which may be a healthcare provider (e.g., doctor, nurse, technician, etc.) device. Computing device 120 may be any suitable computing device such as a desktop, laptop, smartphone, tablet, wearable, smart device, or the like. Computing device 120 may set operating parameters for external controller 104 to drive implantable pump 102.

Patient device 130 may be used by the patient or any other user (e.g., caretaker of the patient) and may similarly communicate with external controller 104 via any well-known wired or wireless connection. Patient device 130 may be any suitable computing device such as a desktop, laptop, smartphone, tablet, wearable, smart device, or the like. Patient device 130 may receive operational and/or heath information from external controller 104 regarding operation and/or function of implantable pump 102.

Charging device 135 may be a charging device for charging a battery of external controller 104. Charging device 135 may include an electrical interface with external controller 104 for electrical communication with external controller 104. Alternatively, or additionally, charging device 135 may include inductive charging coils which may electronically communicate with inductive charging coils of external controller 104. Charging device 135 may include visual indicators (e.g., LED or digital display) for indicating when charge is complete.

Charging device 135 may further include a processor (e.g., microprocessor) for controlling charging device 135 and/or overseeing communication with external controller 104 and/or implantable pump 101. Additionally, charging device 135 may communicate with patient device 130 and/or computing device 120. In one example, only charging device 135 may communicate with implantable pump 102 and patient device 130 and computing device 120 may communicate with implantable pump 102 via external controller 104. For example, charging device 135 may support Bluetooth and cellular communications and may communicate with external controller 104 via Bluetooth and may communicate with computing device 120 and/or patient device 130 using the Internet over cellular and/or Wi-Fi.

Referring now to FIG. 1B, implantable pump 102 may be implanted in arm 145 of patient 115. Arm 145 of patient 115 may have lymph buildup and patient 115 may have lymphedema. Implantable pump 102 may be positioned in an upper portion arm 145 of patient 115, such as near the shoulder. Implantable pump in FIG. 1B may be connected to inlet catheter 142 and outlet catheter 144. Inlet catheter 142 may be similar to inlet catheter 108 of FIG. 1A but may be sized to fit within arm 145. Outlet catheter 144 may be similar to outlet catheter 110 but may be sized to extend from arm 145 of patient 115 and may be sized to terminate in the clavicle or neck region (e.g., supra-clavicular) of patient 115. External controller 104 may be set using computing device 120 based on certain operational settings to move lymph from arm 145 into the neck or clavicle space of patient 115 to reduce swelling in arm 145.

Figure 2:
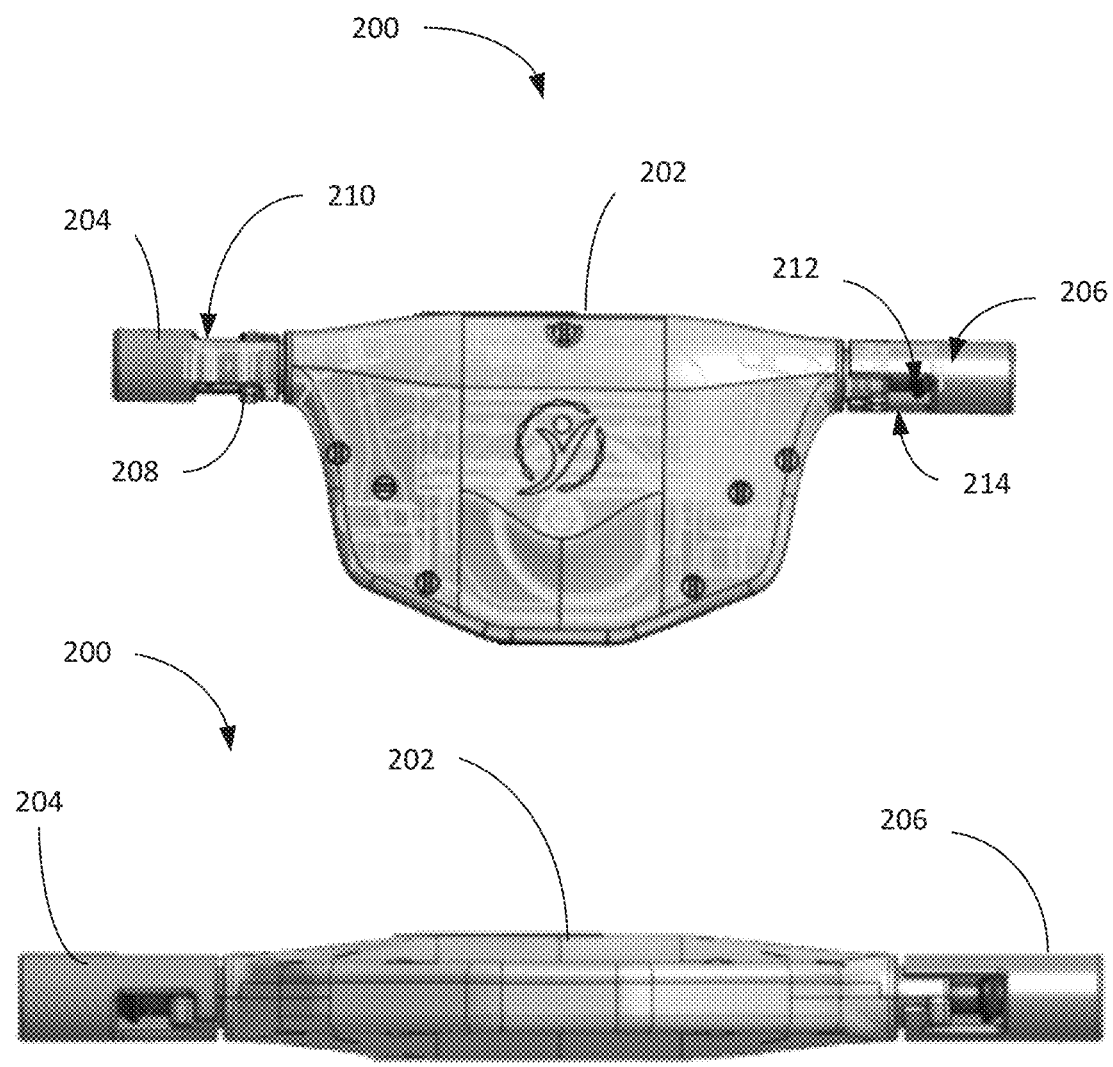
FIG. 2 illustrates front and bottom views of an implantable pump for managing bodily fluid in a patient.

Referring now to FIG. 2, front and bottom views of an implantable pump for managing bodily fluid in a patient are illustrated. Implantable pump 200 may be the same as or similar to implantable pump 102 of FIGS. 1A-1B. Implantable pump 200 may include housing 202 which may be made from any suitable biocompatible material (e.g., titanium, stainless steel, alloy, and/or plastic). Implantable pump 200 may be approximately the size of a coin. For example, implantable pump 102 may be around 51 mm in length, 26 mm in height and around 8 mm in width. Implantable pump 200 may be tapered at the ends and may include beveled edges.

Housing 202 may include two halves that are secured together using threaded engagement (e.g., screws and thread), for example. Implantable pump 200 may include connector 204 which may connect to an outlet end of an inlet catheter and may include connector 206 which may connect to an inlet end of an outlet catheter. Implantable pump 200 may include inlet connector 208 which may include a protrusion. Inlet connector 208 may connect to an inlet tube of implantable pump 200. Connector 204 may include window 210 for receiving the protrusion of inlet connector 208 and may be turned with respect to inlet connector 208 to connector 204 to implantable pump 100. Implantable pump may include outlet connector 212 which may include a protrusion. Outlet connector 212 may connect to an outlet tube of implantable pump 200. Connector 206 may include window 214 for receiving the protrusion of outlet connector 212 and may be turned with respect to outlet connector 212 to connector 206 to implantable pump 200.

Figure 3A:
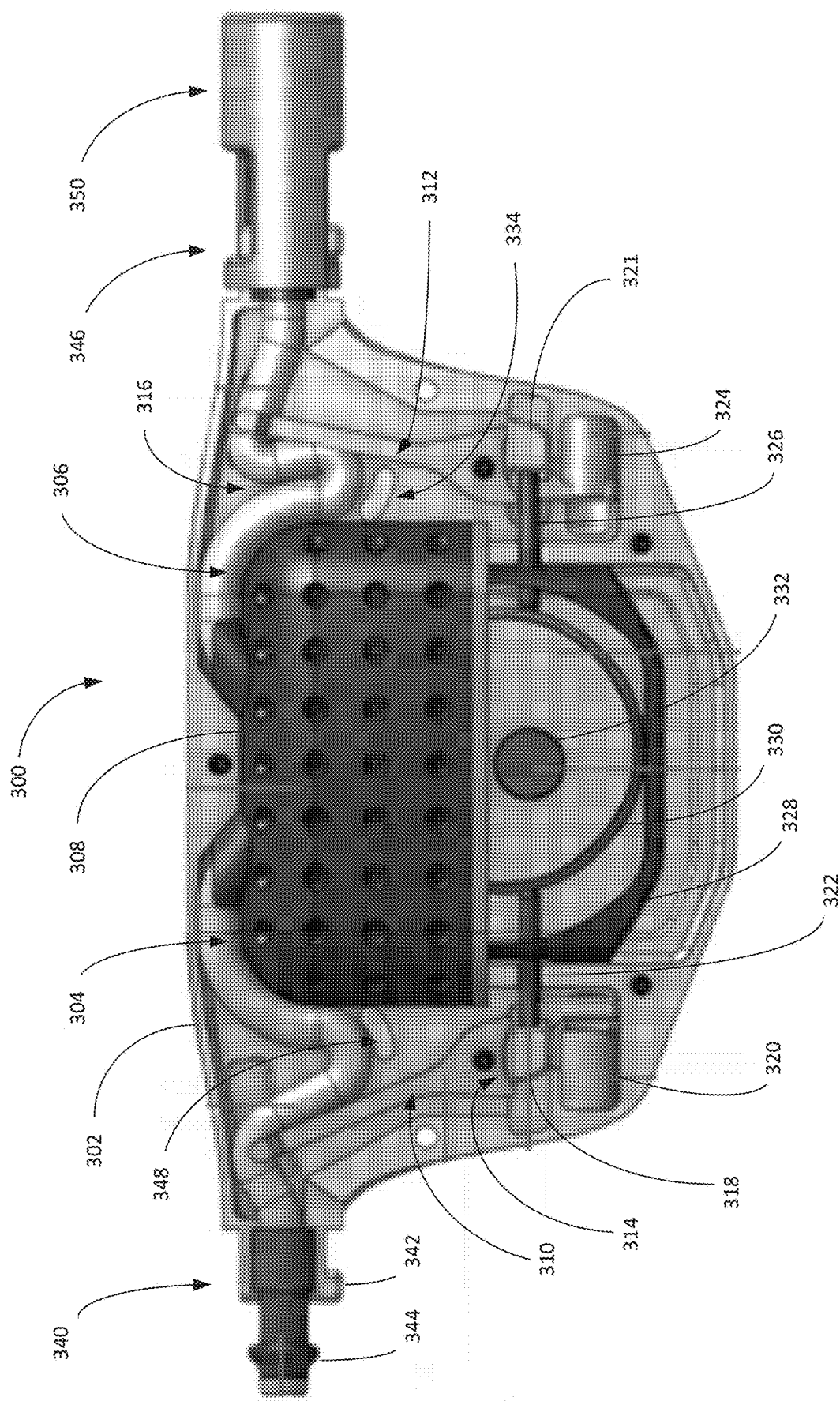
FIGS. 3A-3B illustrate internal views of an implantable pump for managing bodily fluid in a patient.
Figure 3B:
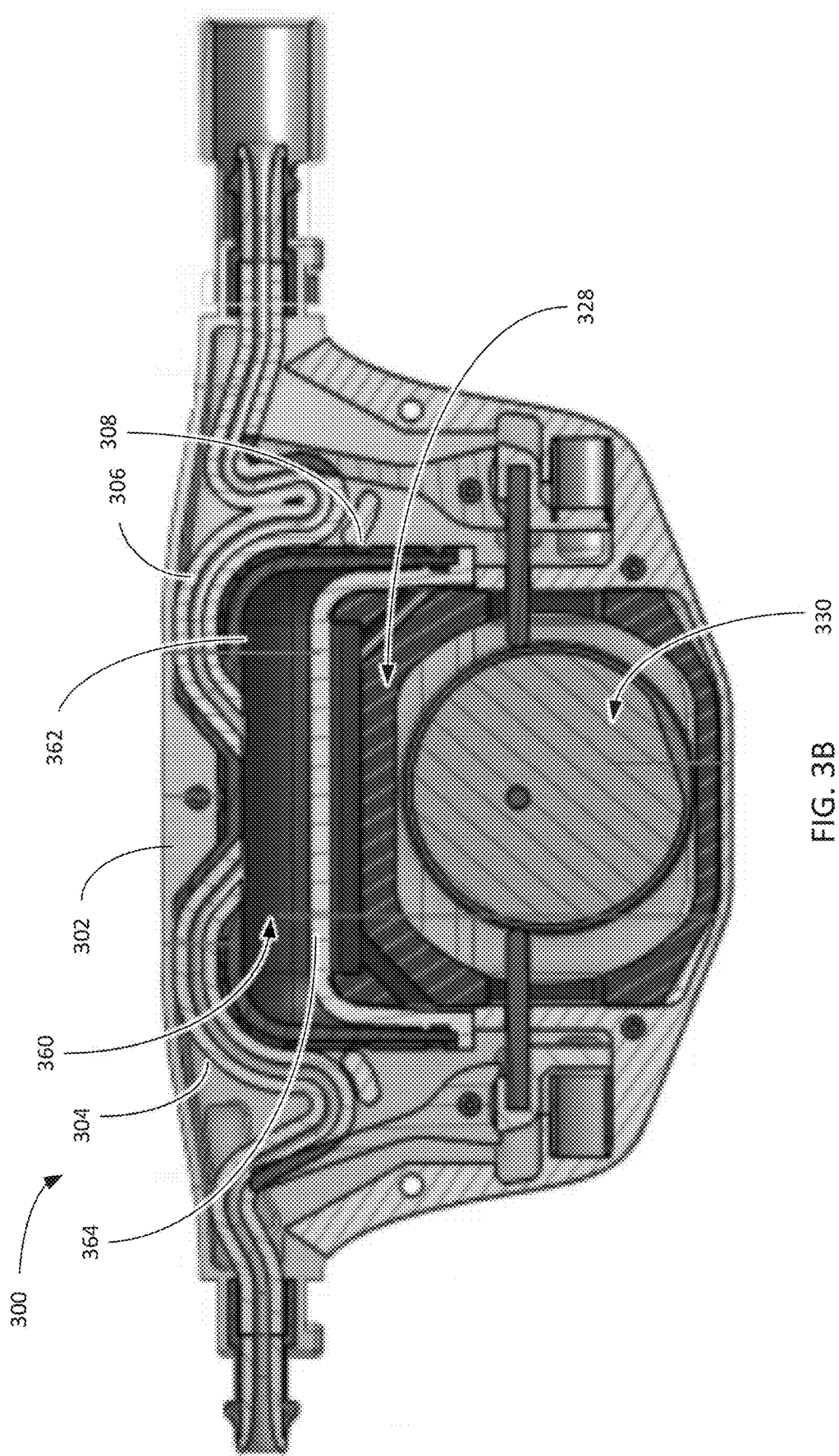

Referring now to FIGS. 3A-3B, internal views of an implantable pump for managing bodily fluid in a patient are illustrated. Implantable pump 300 may be the same or similar to implantable pump 102 of FIGS. 1A-1B. Implantable pump 300 may include housing 302 which may be the same as or similar to housing 202. Inlet tube 304 may be connected to connection portion 340 at an inlet end and may be connected to a fluid chamber at an outlet end. Outlet tube 306 may be connected to the fluid chamber at an inlet end and outlet connector 346 at an outlet end. Membrane shell 308 may be a rigid shell over which inlet tube 304 and outlet tube 306 extend over and enter. The fluid chamber may be positioned within the external shell.

Inlet tube 304 may be positioned within housing 302 such that a portion of inlet tube 304 may interface with lever 310. Protrusion 348 may extend from housing 302 and maintain inlet tube 304 in a curved shape within housing 302. Lever 310 may be hinged to housing 302 at cam interfacing end 314 may have a curved surface for mechanically interfacing with cam 318. Cam 318 may move left and right to cause lever 310 to rotate between an open position and a closed position. Lever 310, protrusion 348, and membrane shell 308 may form a kinking valve and, when lever 310 is in an open position, may permit fluid flow through inlet tube 304 and, when lever 310 is in a closed position such that inlet tube is kinked, fluid flow may be entirely obstructed.

The inlet tube may be kinked when lever 310 causes inlet tube to form a U-shape and the lever compresses inlet tube 304 between lever 310, protrusion 348, and membrane shell 308. The compressive force applied by lever 310 may be applied across a relative large surface area of inlet tube 304 such that inlet tube sufficiently elastically deforms to obstruct fluid flow without damaging inlet tube 304. The kinking valve thus may accomplish an open position in which fluid may flow and a closed position in which flow is prevented from flowing which can prevent fatigue of inlet tube 304, extending the life of implantable pump 300.

Lever 312 may similarly be positioned with respect to outlet tube 306 to mechanically interface with outlet tube 306. For example lever 312 may have a hinged connection to housing 302 at the cam interfacing portion of lever 312. Outlet tube 306 may be positioned in a curved shape by protrusion 334. When lever 312 transitions from an open position to a closed position, outlet tube may be caused to form U-shape 316 and lever 312 may compress outlet tube 306 against membrane shell 308 and protrusion 334 to obstruct fluid flow in outlet tube 306. Lever 312 may be transitioned to an open position to permit fluid to flow through outlet tube 316.

Lever 310 may be transitioned between open and closed positions by cam 318 which may be caused to move by pusher 322. Cam 318 may be biased by elastic component 320 which may be a biasing component and may mechanically interface with cam 318. For example, elastic component 320 may be a spring, foam, or other elastic material or device that compresses and returns to its original shape. Elastic component 320 may bias cam to position lever 310 in an open position such that when lever 310 is in a closed position, lever may be biased by elastic component 320 to return to the open position. In the exemplary position illustrated in FIG. 3A, lever 310 is in the open position and lever 312 is in the closed position.

Lever 312 may similarly be transitioned between open and closed positioned by cam 321, which may be caused to move by pusher 326. Cam 321 may be biased by elastic component 324, which may be a biasing component and may mechanically interface with cam 321 similar to cam 318 and elastic component 320. Pushers 322 and 326 may be moved by rotor 330 which may be a disk shape and may be supported by housing 302 via a pin or similar connection such that rotor 330 may rotate with respect housing 302 about an axis. Connection 332 may be an axis of rotation of rotor 330 and may be eccentric with respect to rotor 330. Rotor may include one or multiple magnetic portions. For example, rotor 330 may include a permanent magnet disk or annular structure. In one example, rotor 330 may include a neodymium permanent magnetic disk that may be coated with parylene and/or ceramic multilayer coating.

As rotor 330 rotates about an eccentric axis, pushers 322 and 326 are caused by rotor 330 to move toward levers 310 and 312 respectively. As rotor 330 rotates further, pushers 322 and 326 may return to their original position and may biased to return to their original positions via elastic component 320 and elastic component 324 acting upon cam 318 and cam 321, respectively, cam 318 may be connected to pusher 322 and cam 321 may be connected to pusher 326.

Rotor 330 may be positioned within piston 328 and/or may directly mechanically interface with piston 328. As rotor 330 is eccentrically connected to housing 302, rotor 330 may move up and down as it rotates and such movement may be translated to piston 328 which may be free to move up and down with respect membrane shell 308, though rotor may be free to rotate within or adjacent to piston 328 to cause piston 328 to move into and out of membrane shell 308.

As shown in FIG. 3A, connection portion 340 may include protrusion 342 and connection portion 340 which may have protrusion 344. Protrusion 342 may not extend 360 degree around connection portion 340. Protrusion 344 may extend 360 degrees. Protrusion 344 may be made from the same (i.e., identical) material as inlet tube 304, or alternatively it may be covered only on the internal surface by the same (i.e., identical) material as inlet tube 304 Similarly, outlet connector 346 may have the same components and structure as inlet connector. As shown in FIG. 3A, connector 350 may extend over protrusion and turn to lock over the protrusion. Connector 350 may attach to an outlet catheter.

Referring now to FIG. 3B, a cross-sectional view of implantable pump 300 is illustrated. As shown in FIG. 3B, inlet tube 304 may have an outlet that is connected to and terminates at fluid chamber 360 and outlet tube 306 may have an inlet that begins at and is connected to fluid chamber 360. Fluid chamber may be formed by membrane shell 308, which may be lined with internal membrane 362.

Inlet tube 304 may be connected to connection portion 340 at an inlet end and may be connected to a fluid chamber at an outlet end. Outlet tube 306 may be connected to the fluid chamber at an inlet end and outlet connector 346 at an outlet end. Internal membrane 362 may line an interior surface of membrane shell and may mate with and/or receive an outlet of inlet tube 304 and an inlet of outlet tube 306. Inlet membrane may be any suitable elastic material such as silicone.

Membrane shell 308 and/or internal membrane 362 may connect at a bottom portion to elastic membrane 364, which may similarly be any suitable elastic material such as silicone. Elastic membrane 364 may form a bottom portion of fluid chamber 360 and membrane shell 308 and internal membrane 362 may form an upper portion of fluid chamber 360 such that fluid may be positioned between elastic membrane 364 and internal membrane 362. Internal membrane 362 may make a sealed connection with elastic membrane 364 to define the fluid chamber. For example, internal membrane 362 and elastic membrane 364 may be adhered to one another or otherwise connected to create a fluid seal. For example, internal membrane 362 and elastic membrane 364 may be hermetically sealed.

Internal membrane 362 may be adhered to or otherwise affixed to an inner surface of membrane shell 308 such that internal membrane 362 may not move with respect to membrane shell. In one example, internal membrane 362 may enter holes of membrane shell 308 to mate to membrane shell 308. However, elastic membrane 364 may be designed to move with respect to membrane shell 308 and internal membrane 362. For example, elastic membrane 364 may be positioned over a top portion of piston 328 and may move upward with piston 328 as piston is moved upward by rotor 330. Elastic membrane 364 may be biased to return to a resting position and thus may move downward with piston 328 as piston 328 moves downward. In this manner, the volume of fluid chamber may decrease as piston 328 moves upward and may increase as piston moves downward. A portion of elastic membrane 364 may be glued or otherwise adhered to piston 328 (e.g., to a top portion of the piston)

such that when piston 328 moves downward during an intake cycle, elastic membrane 364 is caused to move downward with piston 328. While elastic membrane 364 may be adhered to a portion of piston 328, elastic membrane 364 may otherwise be free to stretch with respect to piston 328 as piston 328 moves up and down.

Figure 4A:
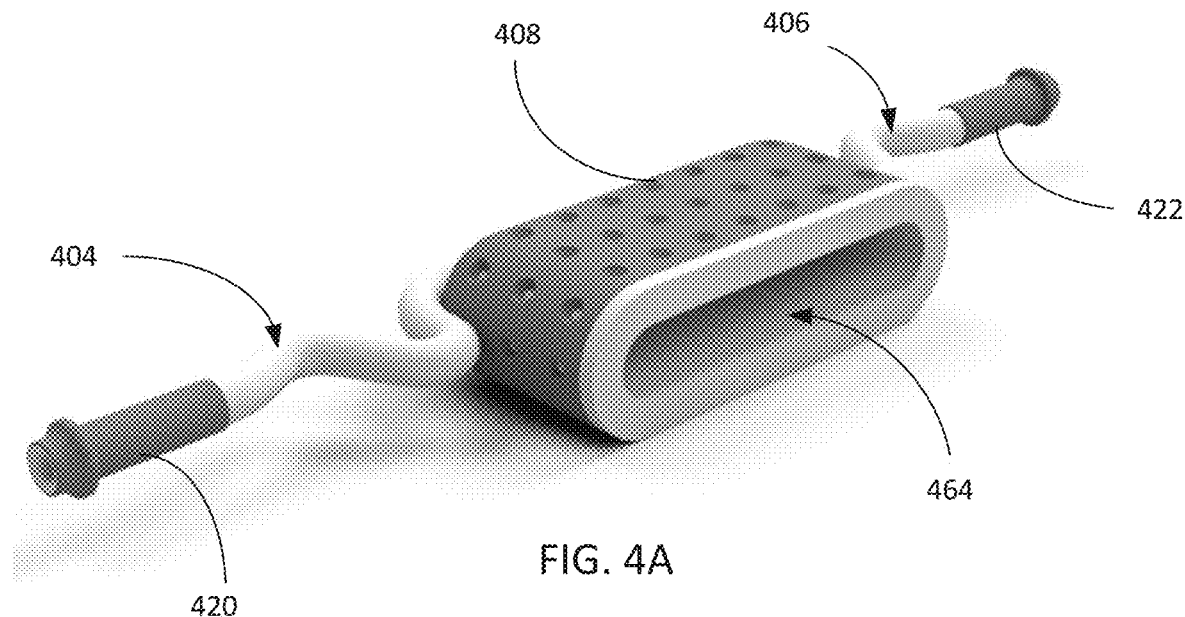
FIGS. 4A-4B illustrate an outer shell, an internal membrane of the outer shell, an elastic membrane, an inlet tube, an outlet tube, and connector portions of an implantable pump.
Figure 4B:
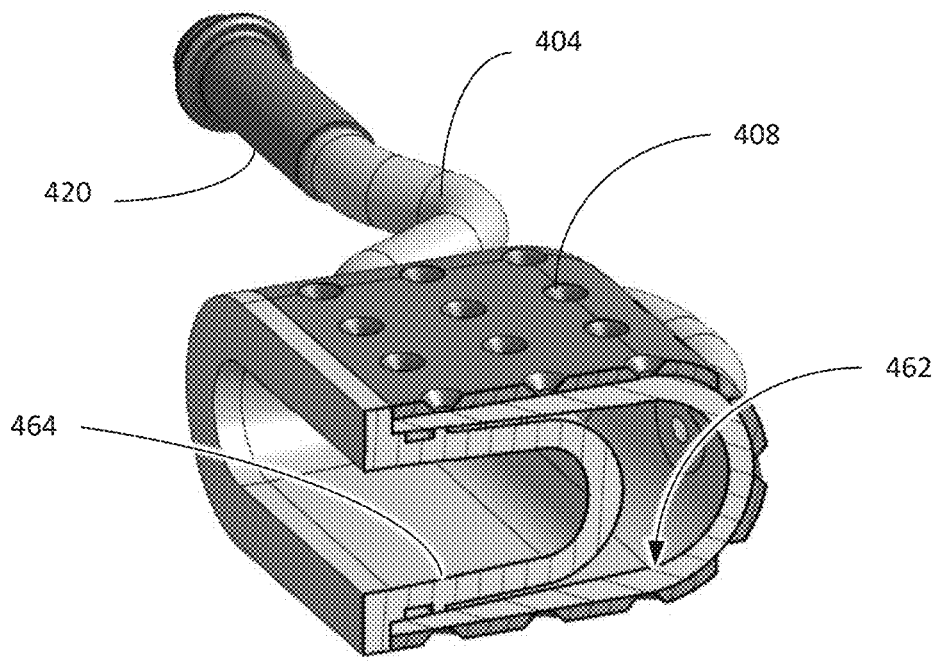

Referring now to FIG. 4A-4B, an outer shell, an internal membrane of the outer shell, an elastic membrane, an inlet tube, an outlet tube, and connector portions of an implantable pump are illustrated. Membrane shell 408, inlet tube 404, and outlet tube 406 may be the same as or similar to membrane shell 308, inlet tube 304, and/or outlet tube 306 of FIGS. 3A-3B, respectively. Additionally, internal membrane 462 and elastic membrane 464 may be the same as or similar to internal membrane 362 and elastic membrane 364 of FIGS. 3A and 3B.

Inlet connector 420 may be connected to or extend form inlet tube 404 and may interface with an inlet catheter. Outlet connector 422 may be connected to or extend from outlet tube 406 and may interface with an outlet catheter. Inlet connector 420, outlet connector 422, inlet tube 404 and outlet tube 406 may be made entirely from the same material (e.g., implantable grade silicone that may be internally coated with a hydrophilic coating (e.g., heparin coating)). Alternatively, inlet connector 420 and outlet connector 422 may be made from a rigid material (i.e., titanium, stainless steel, rigid plastic) and covered on the internal surface by the same material of inlet tube 404 and outlet tube 406 (e.g., implantable grade silicone that may be internally coated with a hydrophilic coating (e.g., heparin coating)). Inlet connector 420 and/or outlet connector 422 may include a protrusion that extends 360 degrees around inlet connector 420 and/or outlet connector 422. Each protrusion may facilitate a fluid seal with respective inlet and outlet catheters.

Figure 5A:
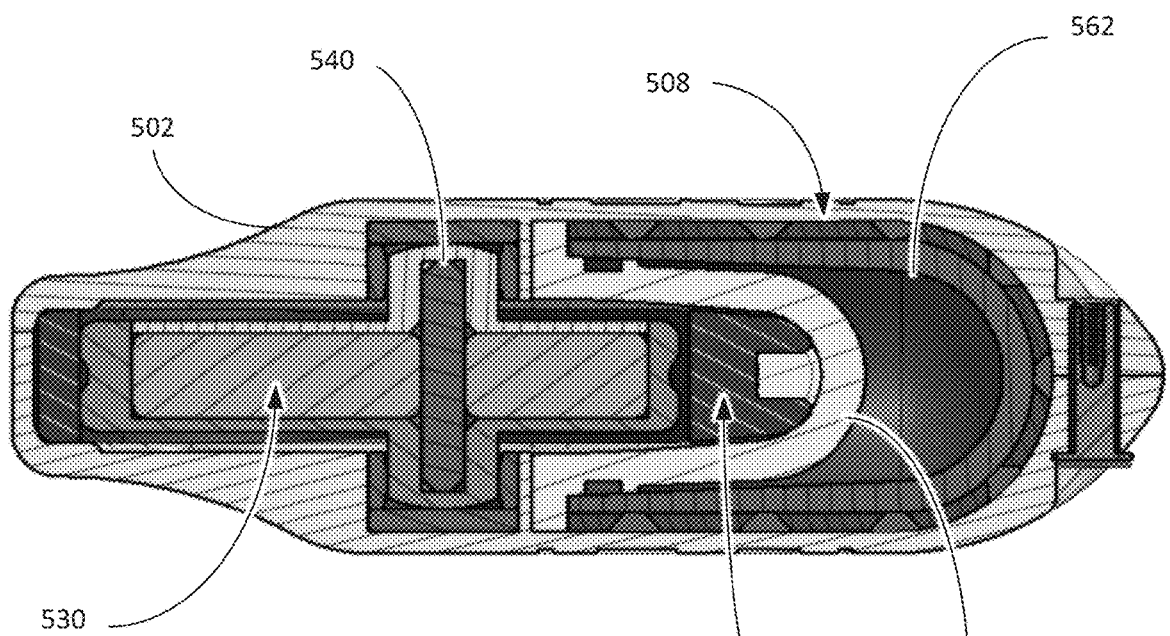
FIGS. 5A-5B illustrate cross-sectional views of the implantable pump showing the fluid chamber in an intake and an discharge position.
Figure 5B:
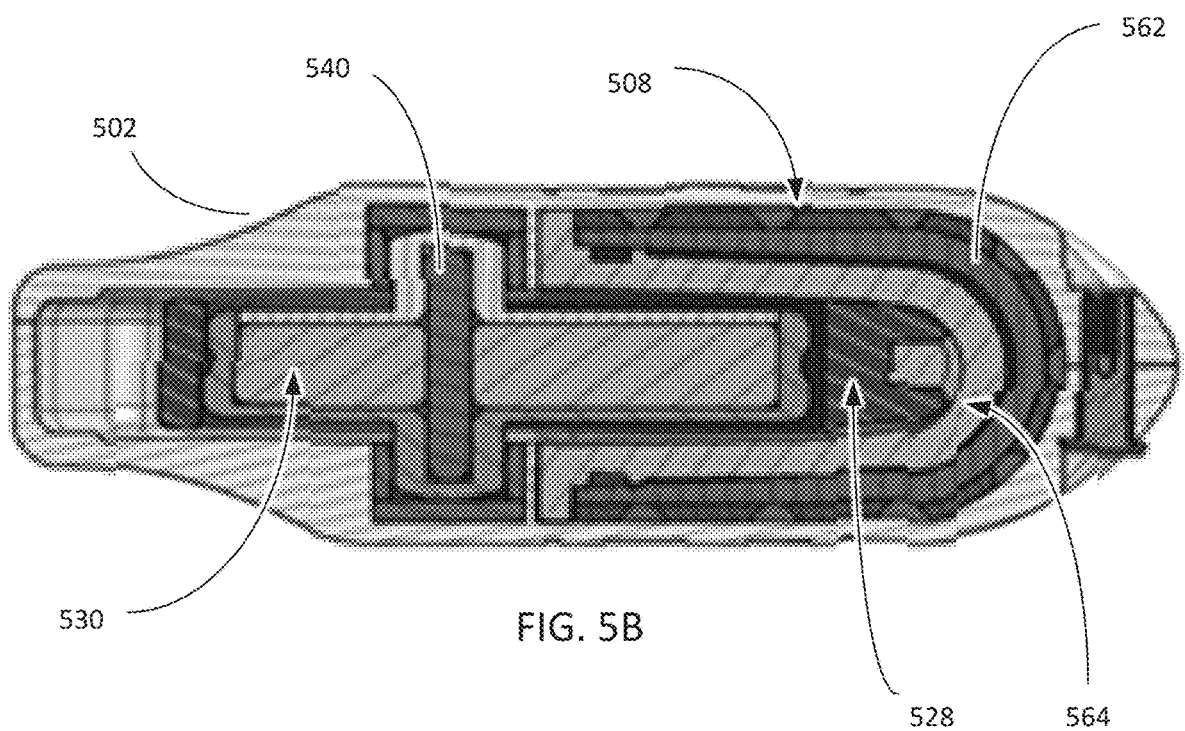

Referring now to FIGS. 5A-5B, a cross-sectional view of the implantable pump showing the fluid chamber in the intake position and the discharge position is illustrated. Implantable pump 500 may be the same as or similar to implantable pump 300 of FIGS. 3A-3B. More specifically, housing 502, membrane shell 508, internal membrane 562, elastic membrane 564, piston 528, and/or rotor 530 may be the same as or similar to housing 302, membrane shell 308, internal membrane 362, elastic membrane 364, piston 328, and/or rotor 330 of FIGS. 3A-3B.

As shown in FIG. 5A, rotor 530 may be rotated about eccentric axis 540 such that piston 528 is in a downward position relative to membrane shell 508, internal membrane 562, and elastic membrane 564. In this downward position of piston 528, the volume of the fluid chamber defined by internal membrane 562 and elastic membrane 564 is at its greatest and optimized for receiving lymph from the inlet tube. The position illustrated in FIG. 5A is referred to as the intake position.

As shown in FIG. 5B, rotor 530 may be rotated about eccentric axis 540 such that piston 528 is in an upward position relative to membrane shell 508, internal membrane 562, and elastic membrane 564. In this upward position of piston 528, the volume of the fluid chamber defined by internal membrane 562 and elastic membrane 564 is at its smallest and optimized for discharging lymph out of the outlet tube. The position illustrated in FIG. 5B is referred to as the discharge position.

Figure 6A:
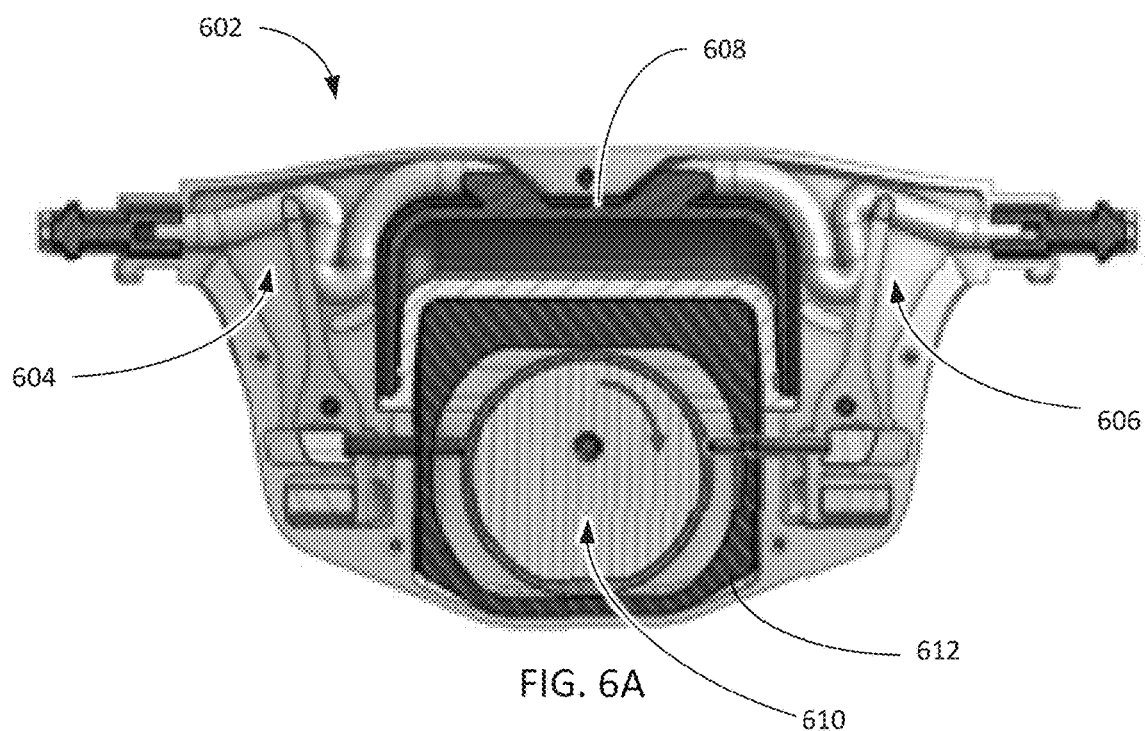
FIGS. 6A-6D illustrate cross-sectional views of the implantable pump showing the implantable pump transition from a discharge cycle to an intake cycle.

Referring now to FIGS. 6A-6D, cross-sectional views of the implantable pump showing the implantable pump transition from a discharge cycle to an intake cycle are illustrated. As shown in FIG. 6A, implantable pump, which may be the same as or similar to implantable pump 300 of FIGS. 3A-3B, is illustrated at the beginning of a discharge cycle. Bodily fluid such as lymph has entered fluid chamber 608 and kinking valve 604 has transitioned to a closed position to prevent the bodily fluid from exiting the fluid chamber out the inlet tube. Kinking valve 606 may remain in a closed position until the rotor begins to rotate further after causing kinking valve 604 to close.

Figure 6B:
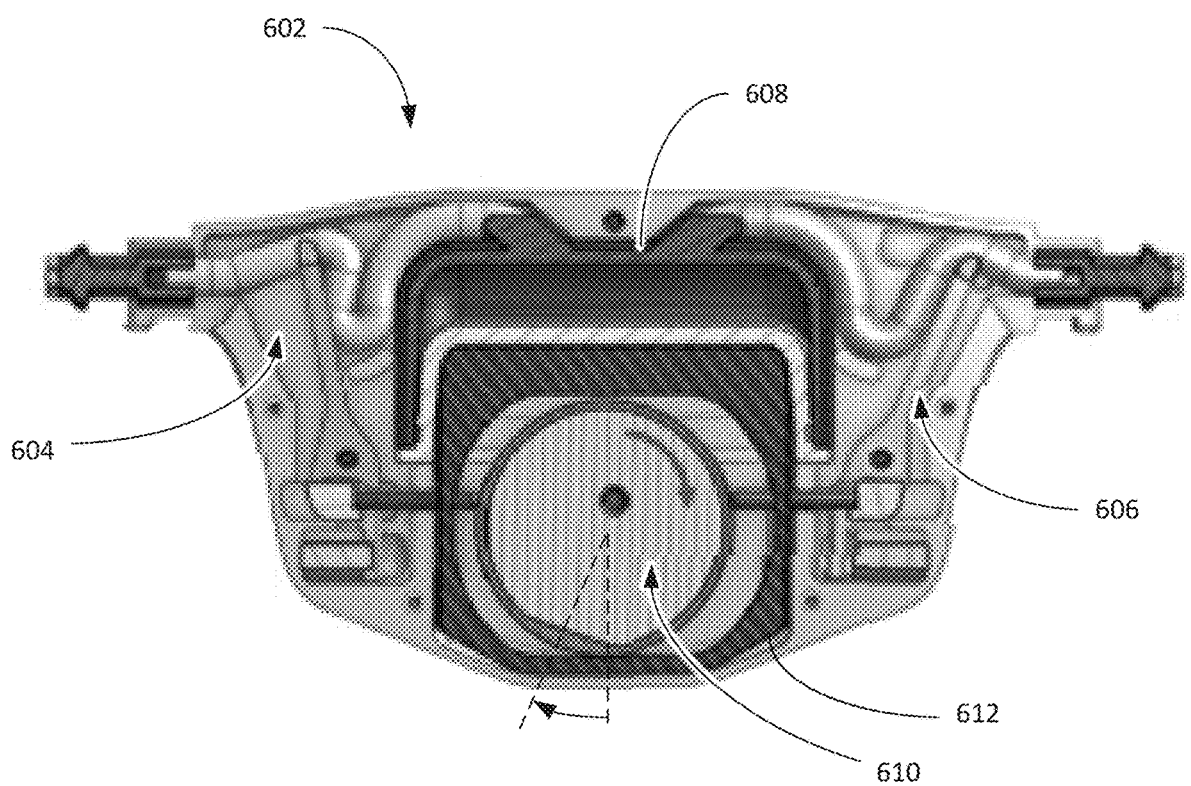

As shown in FIG. 6B, after rotating to cause kinking valve 604 to close, the rotor may continue to rotate (e.g., clockwise), thereby causing kinking valve 606 to open. With kinking valve open in a discharge position, the rotor may continue to rotate to move the piston upwards to thereby reduce the volume of the fluid chamber and cause fluid to exit the outlet tube to discharge the bodily fluid out of the outlet tube. Kinking valve 604 may remain closed as kinking valve 606 is opened during discharge.

Figure 6C:
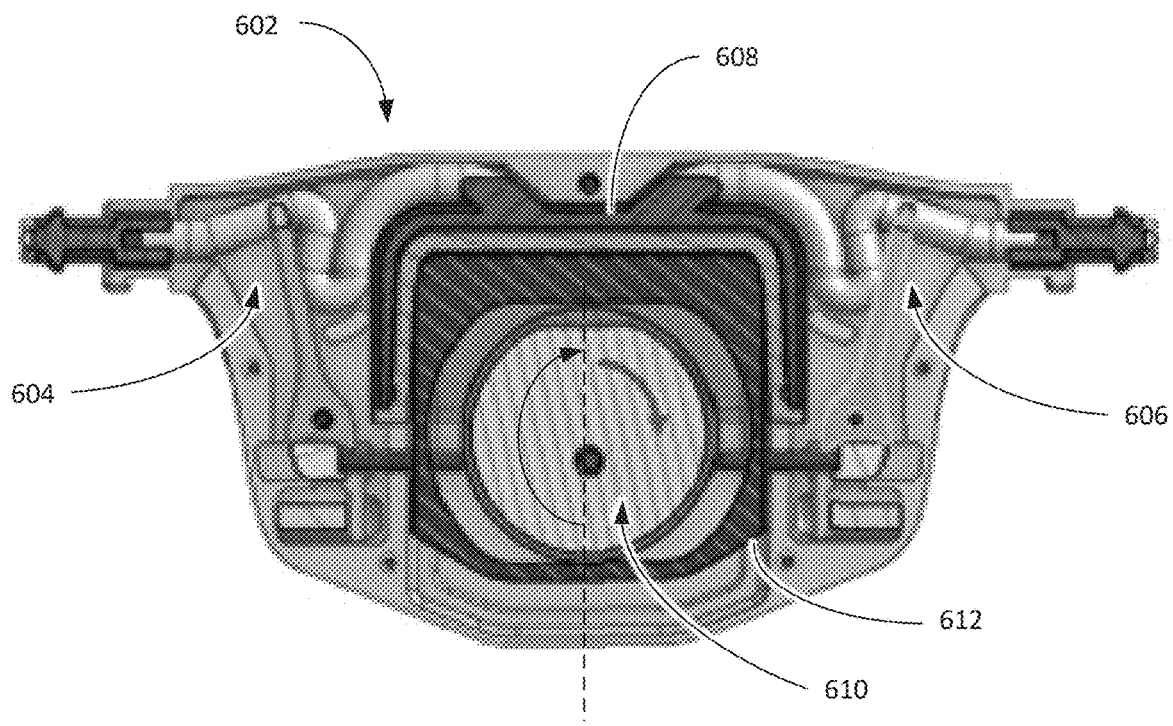
Figure 6D:
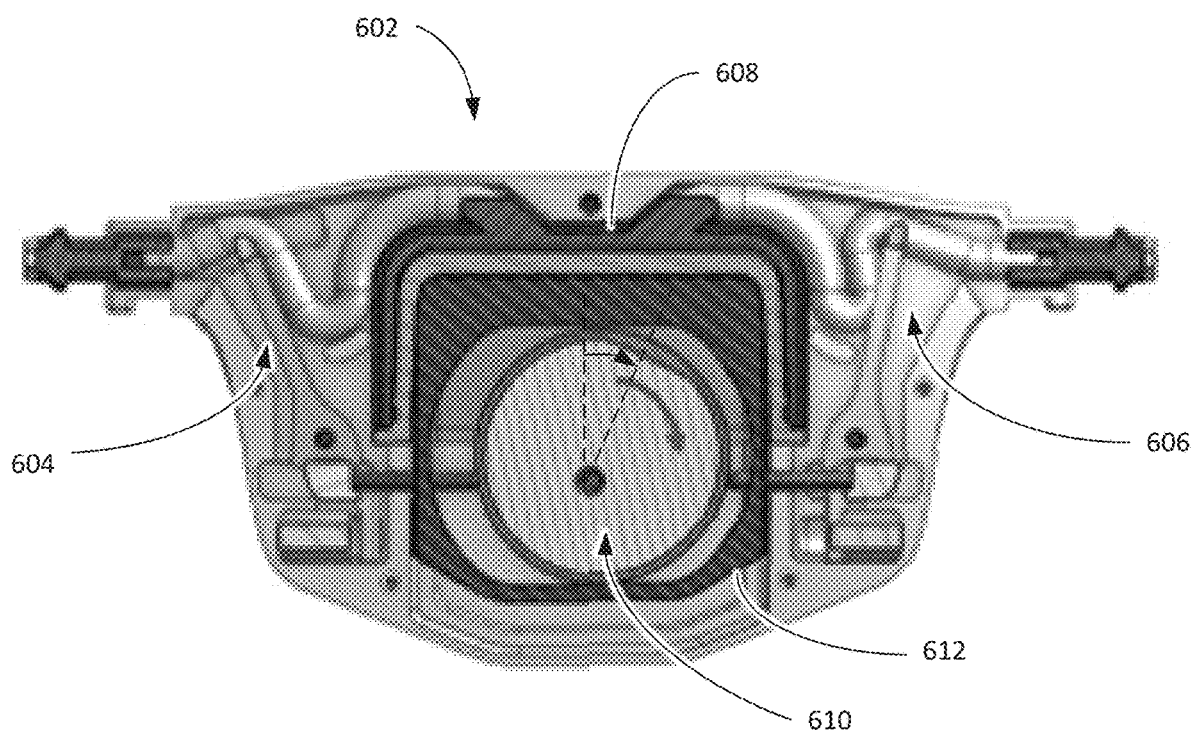

As shown in FIG. 6C, implantable pump 602 is illustrated at the beginning of an intake cycle with piston 612 in a fully upward position to reduce the volume of fluid chamber 608. As rotor 610 rotates to move piston 612 into the fully upward position shown in FIG. 6C, kinking valve 606 closes and kinking valve 604 remains closed. At this point, rotor has rotated 180 degrees from the rotor illustrated in FIG. 6A. In FIG. 6D, rotor 610 may continue to rotate (e.g., clockwise), causing kinking valve 604 to open and causing piston 612 to move downward, resulting in an intake position. Kinking valve 606 may remain closed until piston reaches the rotational position illustrated in FIGS. 6A and 6B. As piston moves downward, fluid chamber 608 may increase in volume resulting in a negative pressure causing bodily fluid to inter the inlet tube via open kinking valve 604.

Figure 7A:
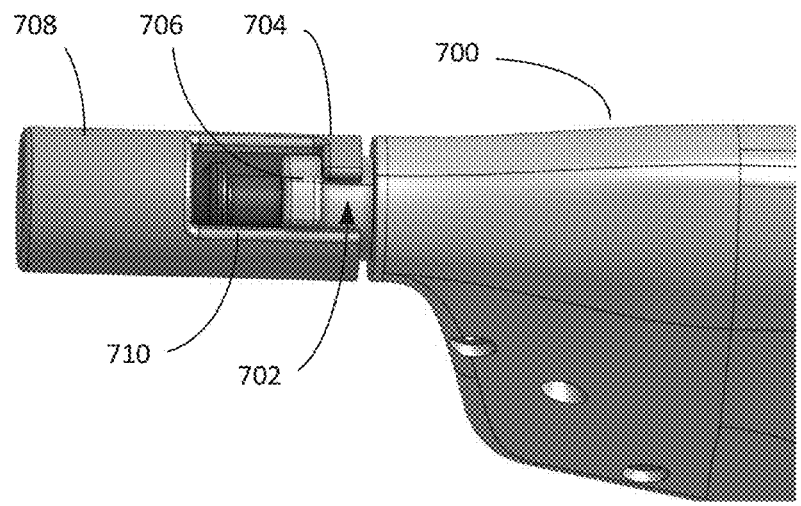
FIGS. 7A-7C illustrate an inlet connector connected at the inlet tube of the implantable pump.
Figure 7B:
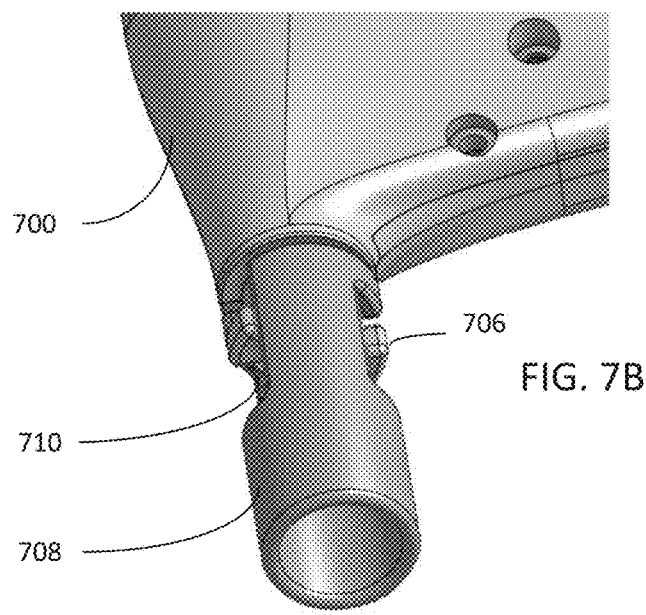
Figure 7C:
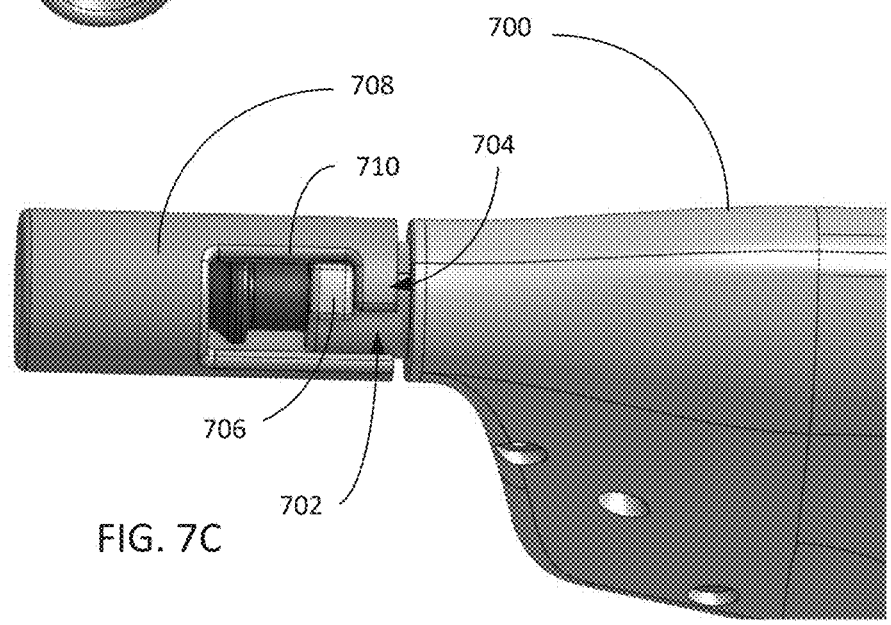

Referring now to FIGS. 7A-7C, an inlet connector connected at the inlet tube of the implantable pump is illustrated. Implantable pump 700 may be the same as or similar to implantable pump 300 of FIGS. 3A-3B and may include inlet connector portion 702 for connecting to inlet connector 708. Inlet connector 708 may be connected to or create a fluid seal with an outlet end of the inlet catheter and/or mate inlet tube with the inlet catheter. Inlet connector portion 702 may include a groove for receiving extension 704 on inlet connector 708. Inlet connector 708 may further include window 710 for receiving protrusion 706 which may extend from an end of inlet connector portion 702. Window 710 may be positioned over protrusion 706 such that extension 704 is positioned into the groove of the inlet connector portion. To lock inlet connector 708 onto inlet connector portion 702, inlet connector portion may be rotated as extension 704 is within the groove of connector portion 702. While inlet connector 708 and inlet connector portion 702 are illustrated in FIGS. 7A-7C, it is understood that the same connector and/or structure of inlet connector portion may connect the outlet catheter to outlet tube.

Figure 8:
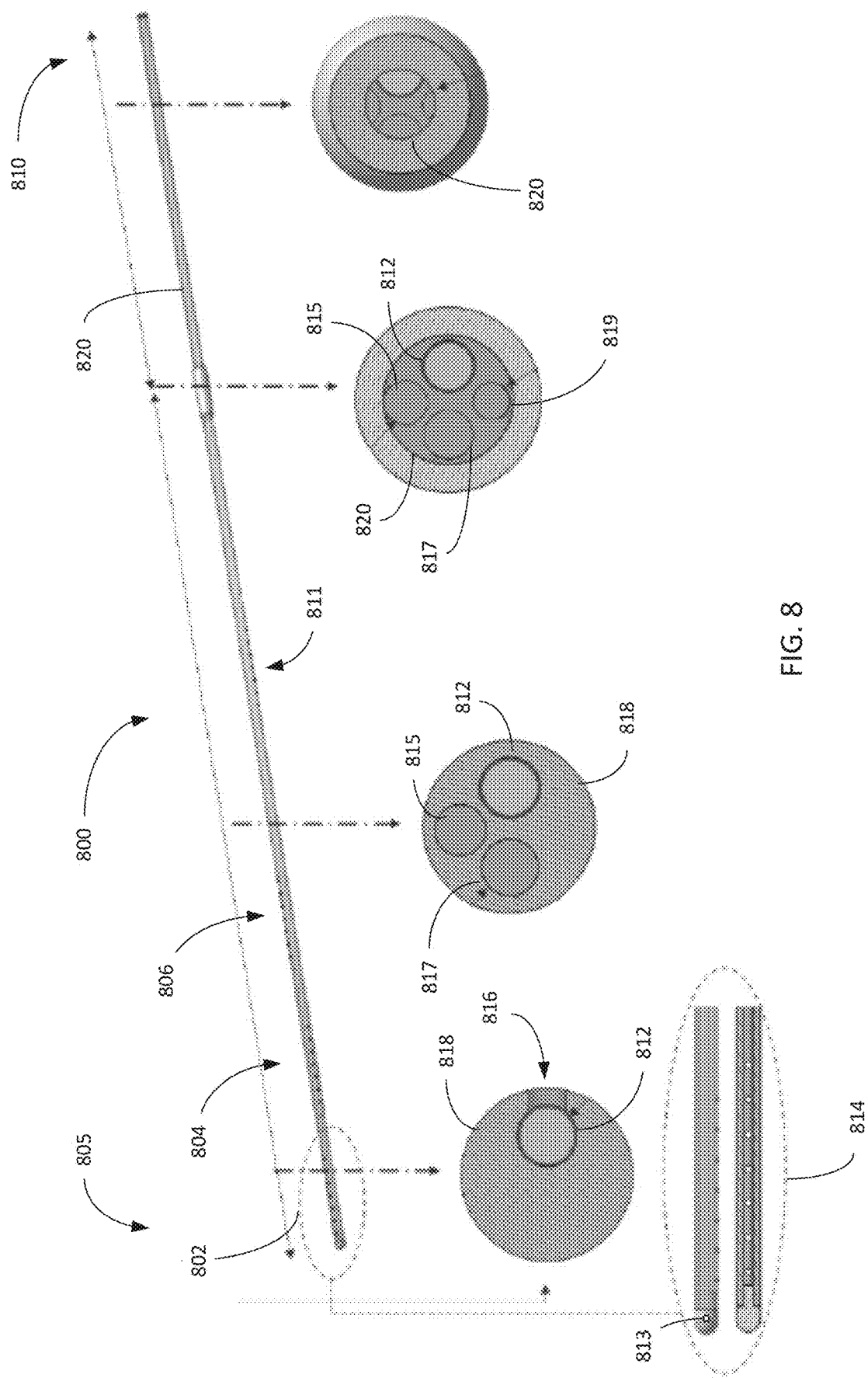
FIG. 8 illustrates the inlet catheter and cross-sectional views of the inlet catheter including various inlet lumens.

Referring now to FIG. 8, the inlet catheter and cross-sectional views of the inlet catheter including various inlet lumens is illustrated. Inlet catheter 800 may be the same as or similar to inlet catheter 108 of FIG. 1B and/or inlet catheter 152 of FIG. 1B. Inlet catheter may include inlet end 805 and outlet end 810. Inlet catheter 800 may include several lumens extending within inlet catheter 800. For example, inlet catheter may include lumens 812, 815, 817 and 819. Alternatively, any number of lumens may be included within inlet catheter 800 (e.g., 1, 2, 3, 5, 6, etc.).

Lumens 812, 815, 817, and 819 may be eccentric with respect to the central axis of inlet catheter and may extend adjacent to one another. At a first end of lumen 812, lumen 812 may connect to holes 802, illustrated in cross-sectional view 814, which may be through holes and/or openings extending through a wall of inlet catheter 800 and may permit bodily fluid to enter through holes 802 (e.g., through hole 816) to enter into lumen 812. Similarly an end of lumens 815, 817 and 819 may connect to holes 804, 806, and 811, respectively, which each may be through holes similar to through hole 816.

Lumen 812 may be longer than lumen 817, which may be longer than lumen 815 which may be longer than lumen 819. Holes 802, 804, 806, and 811 may be positioned on alternating locations along inlet catheter 800 (e.g., each set of holes may be offset circumferentially from the previous set by 90 degrees). The alternating position circumferentially and along the length of inlet catheter 800 may facilitate enhanced retrieval of bodily fluids as such an arrangement offers access to multiple different bodily sites along inlet catheter.

Each of lumens 812, 815, 817 and 819 may include an outlet end that terminates at lumen 820, such that bodily fluid is caused to exit lumens 812, 815, 817 and 819 and enter lumen 820. Each of lumens 812, 815, 817 and 819 may be independent of one another and may run side-by-side along inlet catheter 800. As lumen 820 extends toward outlet end 810 of inlet catheter 800, the internal diameter of lumen 820 may reduce, as shown in FIG. 8. Inlet end 805 may further include suture hole 813 for anchoring inlet end 805 of inlet catheter 800 to certain tissue or bodily structure (e.g., via a suture). Outlet end 810 may be connected to an inlet connector for securing outlet end 810 to the implantable pump.

Holes 802, 804, 806 and 810 may be the same size or, alternatively, may vary in size. For example, holes 802, 804, and 806 may vary in size to regulate fluid flow and/or pressure of the bodily fluid along inlet catheter 800. For example, the holes may be sized such that the hydraulic resistance for each lumen is the same. For example, sets of holes may decrease in diameter moving from inlet end 805 to outlet end 810. In another example, the lumen size may vary. For example, lumen 812 may be about 1.34 mm in diameter, lumen 817 may be 1.28 mm in diameter, lumen 815 may be 1.15 in diameter, and lumen 819 may be 1 mm in diameter. Inlet catheter 800 may be made from implantable grade silicone (e.g., NUSIL MED-4750) or the like. The inlet catheter may be coated with a hydrophilic coating (e.g., heparin coating). It is understood that the dimensions for each component of the inlet catheter may vary and/or different materials than those described herein may be used.

Referring now to FIGS. 9A-B, perspective views of outlet catheters including an anchoring portion at an outlet of the outlet catheter is illustrated. Referring now to FIG. 9A, outlet catheter 900 may be the same as or similar to outlet catheter 110 of FIG. 1A and/or outlet catheter 144 of FIG. 1B. Outlet catheter may include inlet end 904 and outlet end 906. Outlet catheter 900 may include a single central lumen that extends the length of outlet catheter 900 having an outer diameter of about 4 mm an inner diameter of about 2 mm, for example. Inlet end 904 may be connected to the outlet tube (e.g., outlet tube 406 of FIG. 4A) of the implantable pump via an outlet connector. Outlet catheter 900 may include adhesion portion 902 for anchoring the inlet catheter to a portion of the body. For example, adhesion portion 902 may be a polyurethane mesh for adhesion. Outlet end 906 of outlet catheter 900 may optionally be secured to a portion of the body (e.g., via a suture). Referring now to FIG. 9B, outlet catheter 901 may be the same as or similar to outlet catheter 110 of FIG. 1A and/or outlet catheter 144 of FIG. 1B. Outlet catheter 901 may include inlet end 905 and outlet end 908 and outlet catheter may include a single central lumen that extends the length of outlet catheter 901. Outlet catheter 907 may include butterfly feature 907, including two suturing holes, which may be used for anchoring inlet end 905 of outlet catheter 901 to a portion of the body. Outlet end 908 of outlet catheter 901 may optionally be secured to a portion of the body (e.g., via a suture). Outlet catheter 900 and/or outlet catheter 901 may be made from implantable grade silicone (e.g., NUSIL MED-4750) or the like. Outlet catheter 900 and/or outlet catheter 901 may be coated with a hydrophilic coating (e.g., heparin coating). It is understood that the dimensions for each component of outlet catheter 900 and/or outlet catheter 901 may vary and/or different materials than those described herein may be used.

Figure 10A:
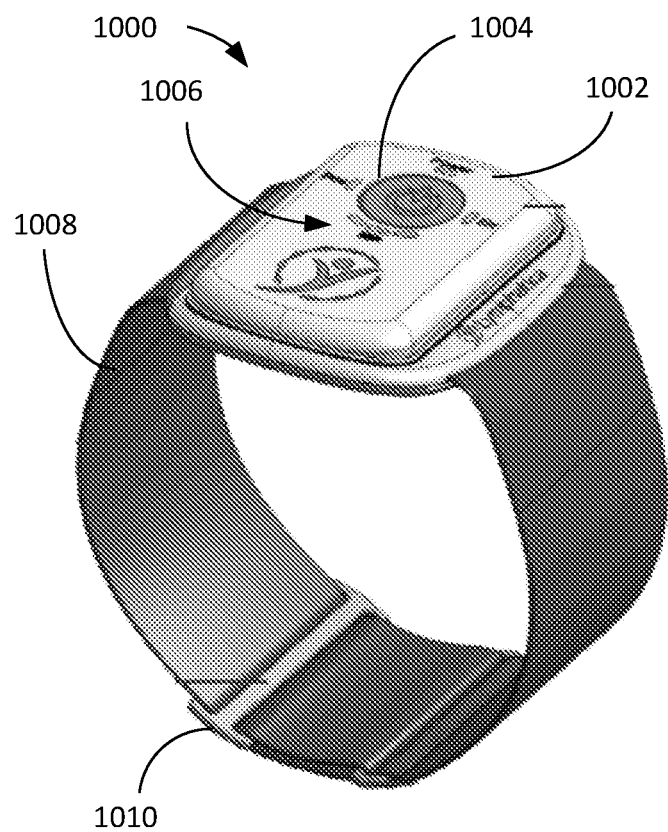

Referring now to FIGS. 10A-10B, perspective and exploded views of the external controller used together with the implantable pump to pump bodily fluid such as lymph is illustrated. Referring now to FIG. 10A, external controller 1000 is illustrated, which may be the same as or similar to external controller 104 of FIG. 1. External controller 1000 may include control unit 1002, and strap 1008 which may be connected to control unit 1002 and may be designed to secure external controller 1000 to a limb of a user (e.g., arm, leg, etc.). Control unit 1002 may include user engagement portion 1004, which may be a button or any other input feature for controlling and/or operating external controller 1000. Control unit 1002 may further include visual indicators 1006 which may provide visual information to the user (e.g., one or more light and/or display).

Referring now to FIG. 10B, an exploded view of the external controller. As shown in FIG. 10B, external controller 1000 may include upper housing 1012 and lower housing 1034 which together may provide the housing for the control unit. Engagement portion 1004, which may be a button and/or toggle, may be positioned in an opening of the housing. Printed circuit board (PCB) 1014 may be positioned immediately below upper housing 1012 and may be connected to button 1004 and may oversee user interface interactions with the user. PCB 1014 may include one or more hall sensors for monitoring the angular velocity of the driving magnet 1016. PCB 1032 may include one or more hall sensors for generating alignment information with the magnetic portion of the implantable pump. Driving magnet 1016, which may be or may include a permanent magnet or disk magnet, may be positioned within bearing 1020, which may facilitate low-friction rotation of driving magnet 1016.

Bearing 1020 may be positioned within wheel 1026 which may be a geared wheel having teeth along an exterior perimeter. A motor assembly including motor 1028, screw 1024 and frame 1022 may cause rotation of driving magnet 1016. For example, motor 1028 may be a DC motor and may include a transmission. Motor 1028 may be connected to screw 1024 and may cause screw 1024 to rotate. Screw 1024 may be any suitable screw shape having threads and designed to rotate about its longitudinal axis. For example, screw 1024 may a worm screw or the like. Frame 1022 may be circular in shape and may receive and/or maintain wheel 1026 and may position wheel 1026 in constant contact with screw 1024 such that the teeth of wheel 1026 remain engaged with the threads of screw 1024. As motor 1028 causes screw 1024 to turn, screw 1024 will cause wheel 1026 to turn thereby turning driving magnet 1016. The rotational speed of driving magnet 1016 may thus be selectively varied using motor 1028.

Printed circuit board (PCB) 1027 may be positioned around, below and/or adjacent to wheel 1026. Printed circuit board 1027 may include one or more hall sensors for generating alignment information with the magnetic portion of the implantable pump. Hall sensors 1030 may additionally be positioned around, below, and/or adjacent to wheel 1026 and may be used for generating alignment information with the magnetic portion of the implantable pump to align driving magnet 1016 with the magnet portion of the implantable pump. Printed circuit board (PCB) 1032 may be positioned between upper housing 1012 and lower housing 1034. PCB 1032, PCB 1027, and/or PCB 1014 may include electronics to control the operation and function of external controller 1000. Charge pins 1036 may be connected to PCB 1032 and may extend through lower housing 1034 to make an electrical connection with a charging device (e.g., charging device 135 of FIG. 1).

Referring now to FIGS. 10C, the motor assembly including motor 1028, the screw, and frame 1022 are illustrated. Driving magnet 1016 and bearing 1020 are illustrated positioned within frame 1022. The wheel may be positioned within frame 1022 and may be rotated by the screw to cause driving magnet 1016 to rotate. Referring now to FIG. 10D, a cut-away view of motor assembly including motor 1028, screw 1024, and the frame are illustrated. FIG. 10D further illustrates wheel 1026 and driving magnet 1016 positioned within and/or adjacent to driving magnet 1016. Screw 1024 may be driven by motor 1028 to rotate threads of screw 1024 which, as shown in FIG. 10D, directly interface with the teeth of wheel 1026 to rotate wheel and driving magnet 1016. PCB 1027 may be generally circular in shape and be positioned adjacent to and/or below wheel 1026 and driving magnet 1016. In one example, the external controller may be the same as or similar to the external controller described in more detail in U.S. Patent Application Publication No. 2020/0197675, published on Jun. 25, 2020, the entire contents of each of which are incorporated herein by reference.

Figure 11:
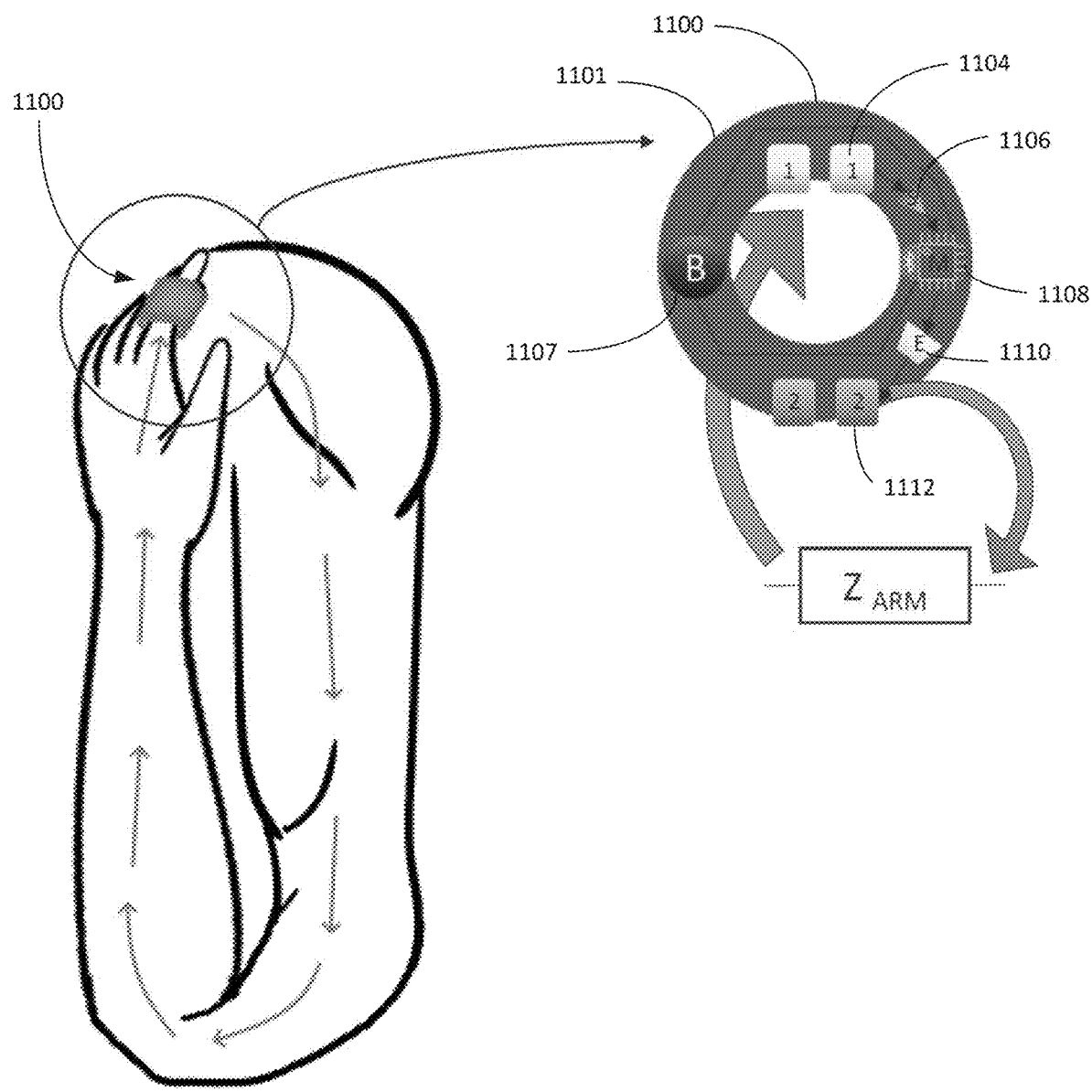
FIG. 11 illustrates a bioimpedance measurement device which may be worn a finger of the patient.

Referring now to FIG. 11, a bioimpedance measurement device which may be worn a finger of the patient is illustrated. Bioimpedance measurement device 1100 device may be annular in shape and may be sized to fit over the finger of a patient. As shown in FIG. 11, bioimpedance device 1100 may be used to measure the bioimpedance of a user's arm for example. The bioimpedance of a user's arm may refer to the effective resistance of an electrical current through the user's arm. The bioimpedance measurement before and after treatment of an arm using the bodily fluid drainage system (e.g., bodily fluid drainage system 100) may be informative with respect to the efficacy of the treatment.

Bioimpedance measurement device 1100 may include annular structure 1101 which may be a rigid, cloth, or elastic annular structure. Bioimpedance measurement device 1100 may include sensing electrodes 1104 and excitation electrodes 1122 which may each be one, two, or more electrodes for contacting the skin the user. Sensing electrodes may be in electrical communications with sensing circuit 1106, which may be in electrical communication with microcontroller unit 1108. Microcontroller unit 1108 may be in electrical communication with excitation circuit 1110, which may be in electrical communication with excitation electrodes 1112. Microcontroller unit 1108 may work together with sensing circuit 1106 and excitation circuit 1110 to cause excitation electrodes to generate an excitation signal and to receive a signal corresponding to the excitation signal from sensing electrodes 1104, which may be an impedance measurement for the user's arm. Bioimpedance measurement device 1100 may further include battery 1107 to power the components of bioimpedance measurement device 1100.

Figure 12:
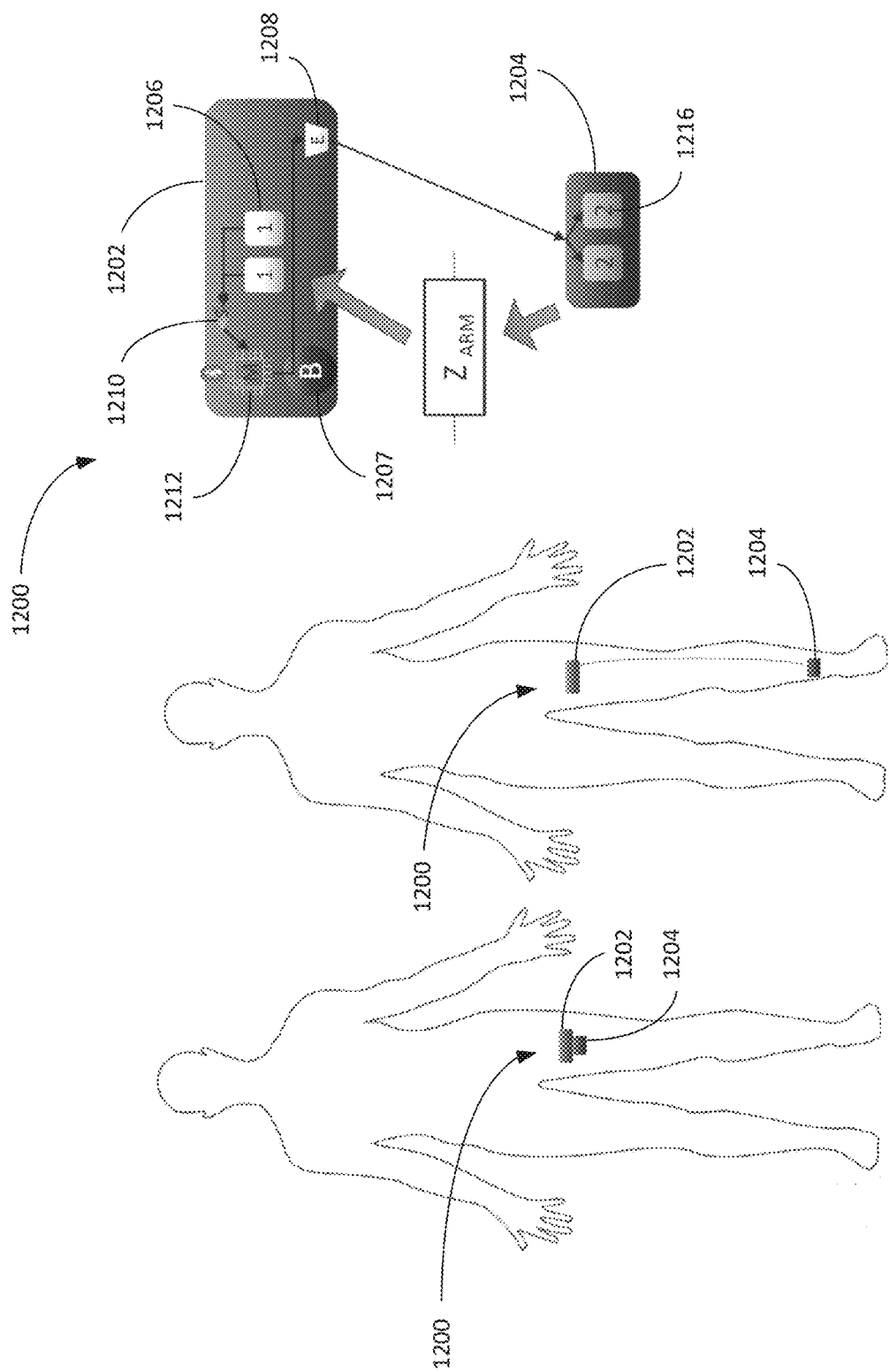
FIG. 12 illustrates a bioimpedance measurement device which may be worn a leg of the patient.

Referring now to FIG. 12, a bioimpedance measurement device which may be worn a leg of the patient us illustrated. Bioimpedance measurement device 1200 may include sensing device 1202 and excitation device 1204, which may be connected to sensing device 1202 via a wired connection. Sensing device 1202 and excitation device 1204 may be positioned adjacent to one another or separated from one another.

Sensing device 1202 may include sensing electrodes 1206 which may each be one, two, or more electrodes for contacting the skin the user. Similarly, excitation device may include excitation electrodes 1216 which may include one, two, or more electrodes for contacting the skin the user. Sensing electrodes 1206 may be in electrical communications with sensing circuit 1210, which may be in electrical communication with microcontroller unit 1212. Microcontroller unit 1212 may be in electrical communication with excitation circuit 1110, which may be in electrical communication with sensing circuit 1210. Microcontroller unit 1212 may work together with sensing circuit 1210 and excitation circuit 1208 to cause excitation electrodes 1216 to generate an excitation signal and to receive a signal corresponding to the excitation signal from sensing electrodes 1206. The impedance measurement for the user's leg may be based on the signal received by sensing electrodes 1206. Bioimpedance measurement device 1200 may further include battery 1207 to power the components of bioimpedance measurement device 1200.

Figure 13:
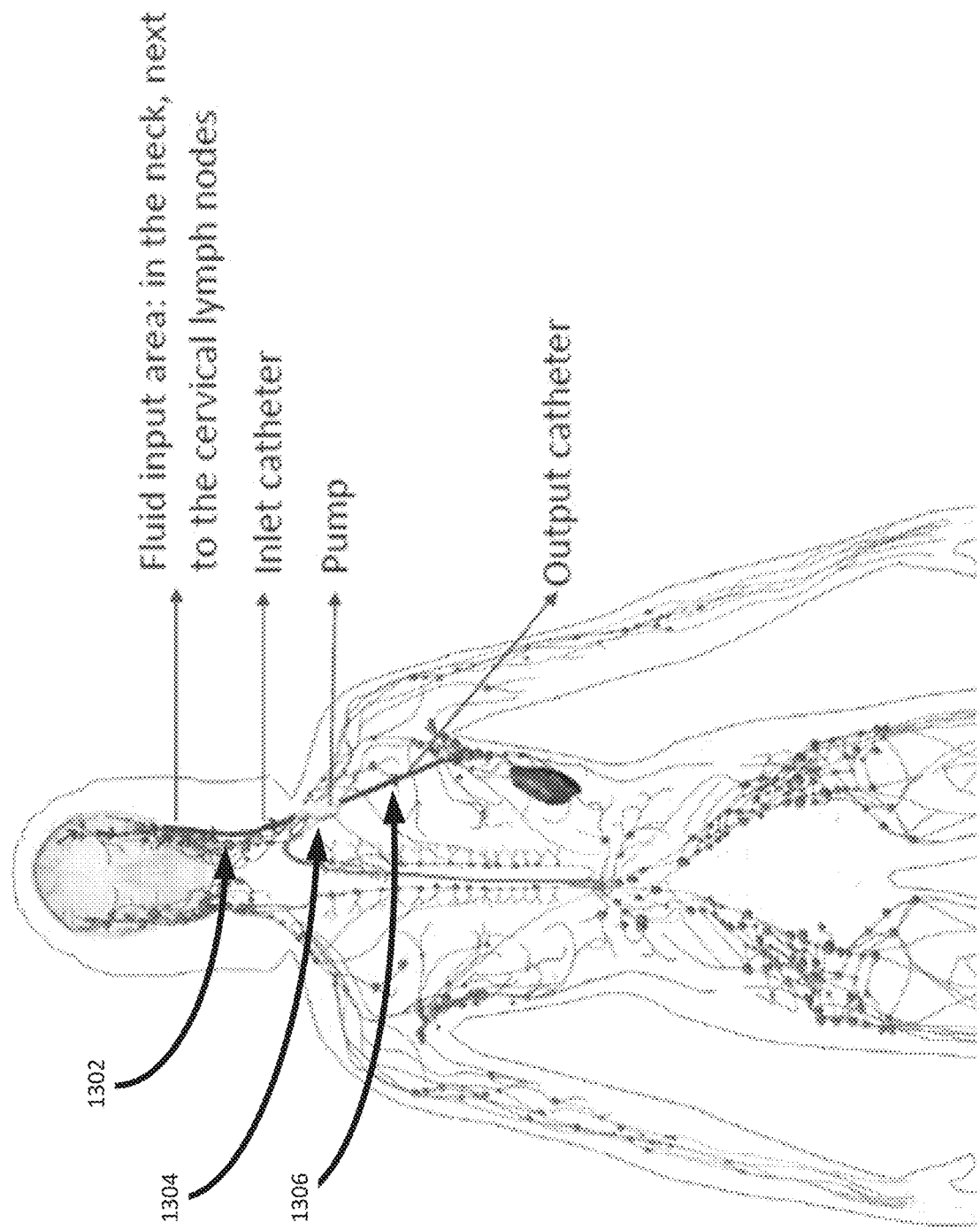
FIG. 13 illustrates a bodily drainage system implanted in a patient's neck area for managing lymph build-up from the cervical, occipital, and/or posterior auricolar lymph nodes.

Referring now to FIG. 13, a bodily drainage system implanted in a patient's neck area for managing lymph build-up from the cervical lymph nodes is illustrated. As shown in FIG. 13, a bodily fluid drainage system which may be the same as or similar to bodily fluid drainage system 100 of FIG. 1 may be implanted near the user's neck area. The bodily fluid drainage system may include implantable pump 1304, which may be the same as or similar to implantable pump 102 of FIG. 1 and may include inlet catheter 1302 and outlet catheter 1306, which may be the same as or similar to inlet catheter 800 of FIG. 8 and outlet catheter 900 of FIG. 9, respectively. As shown in FIG. 13, inlet catheter 1302 may be positioned in the neck area, near the cervical lymph nodes. For example, inlet of the inlet catheter may be cannulated in a lymphatic in the cervical area or an accessible higher lymphatic vessel to increase a flow rate from a cervical lymphatic vessel. The lymphatic may be an upper left or right jugular lymphatic trunk, for example. In one example, inlet catheter 1302 may be in fluid communication with a cervical, occipital, and/or posterior auricular area.

Implantable pump 1304 may be implanted near the user's neck and may create a negative pressure in the neck area near an inlet of inlet catheter 1302. As lymph moves into inlet catheter 1302 due to the negative pressure, lymph may be guided downward away from the brain lymphatics. For example, activating the pump may locally decrease interstitial pressure in the cervical, occipital, and/or posterior auricular area where lymph nodes and lymphatic vessels are located to increase lymphatic flow from the brain via the inlet tube and the outlet tube.

As shown in FIG. 13, the implantable pump 103 may be positioned in the lower neck (e.g., near the collar area) and outlet catheter 1306 may be positioned in an axillary region to be absorbed by the user's axillary lymph nodes. It is understood, however, that implantable pump 1304 may be placed in any other body location and outlet catheter 1306 may be placed in any other region of the body that have functional lymph nodes, with the exclusion of the cervical nodes. Alternatively, or additionally, the outlet of the outlet catheter may be positioned such that it is in fluid communication with a lymphatic duct such as a thoracic or right lymphatic duct, a lymphatic trunk, or is otherwise placed subcutaneously in a subclavian area.

Figure 14:
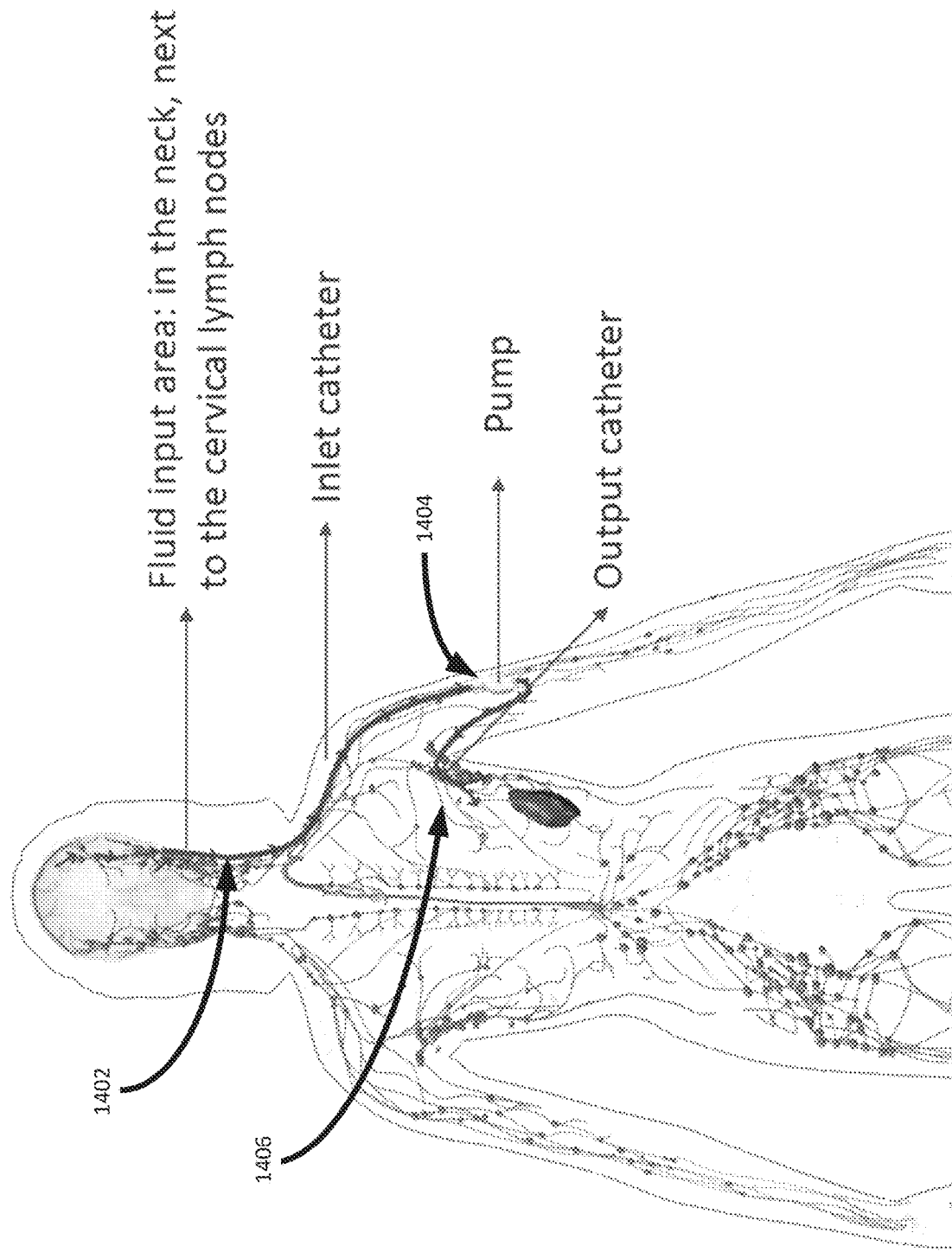
FIG. 14 illustrates a bodily drainage system implanted in a patient's arm for managing lymph build-up from the cervical, occipital, and/or posterior auricolar lymph nodes.

Referring now to FIG. 14, a bodily drainage system is illustrated implanted in a patient's arm for managing lymph build-up from the cervical lymph nodes. As shown in FIG. 14, a bodily fluid drainage system which may be the same as or similar to bodily fluid drainage system 100 of FIG. 1. The bodily fluid drainage system may include implantable pump 1404, which may be the same as or similar to implantable pump 102 and may include inlet catheter 1402 and outlet catheter 1406, which may be the same as or similar to inlet catheter 800 of FIG. 8 and outlet catheter 900 of FIG. 9, respectively. Implantable pump 1404 may be implanted in the user's arm.

As shown in FIG. 14, inlet catheter 1402 may be positioned in the neck area, near the cervical lymph nodes. For example, inlet of the inlet catheter may be cannulated in a lymphatic in the cervical area or an accessible higher lymphatic vessel to increase a flow rate from a cervical lymphatic vessel. The lymphatic may an upper left or right jugular lymphatic trunk, for example. Outlet catheter may be positioned in an axillary region to be absorbed by the user's axillary lymph nodes. In another example, inlet catheter 1302 may be in fluid communication with a cervical, occipital, and/or posterior auricular area and/or the outlet of the outlet catheter may be positioned such that it is in fluid communication with a lymphatic duct such as a thoracic or right lymphatic duct, a lymphatic trunk, or may otherwise be placed subcutaneously in a subclavian area.

Implantable pump 1404 may create a negative pressure in the neck area via inlet catheter 1402, causing a downward lymphatic flow from the brain lymphatics. For example, activating the pump may locally decrease interstitial pressure in the cervical, occipital, and/or posterior auricular area where lymph nodes and lymphatic vessels are located to increase lymphatic flow from the brain via the inlet tube and the outlet tube. A bracelet can be used to drive the pump, similar to the external controller illustrated in FIG. 1A. The output of the lymph may be absorbed by the axillary lymph nodes. It is understood, however, that implantable pump 1304 may be placed in any other body location and outlet catheter 1306 may be placed in any other region of the body have functional lymph nodes, with the exclusion of the cervical nodes.

Figure 15:
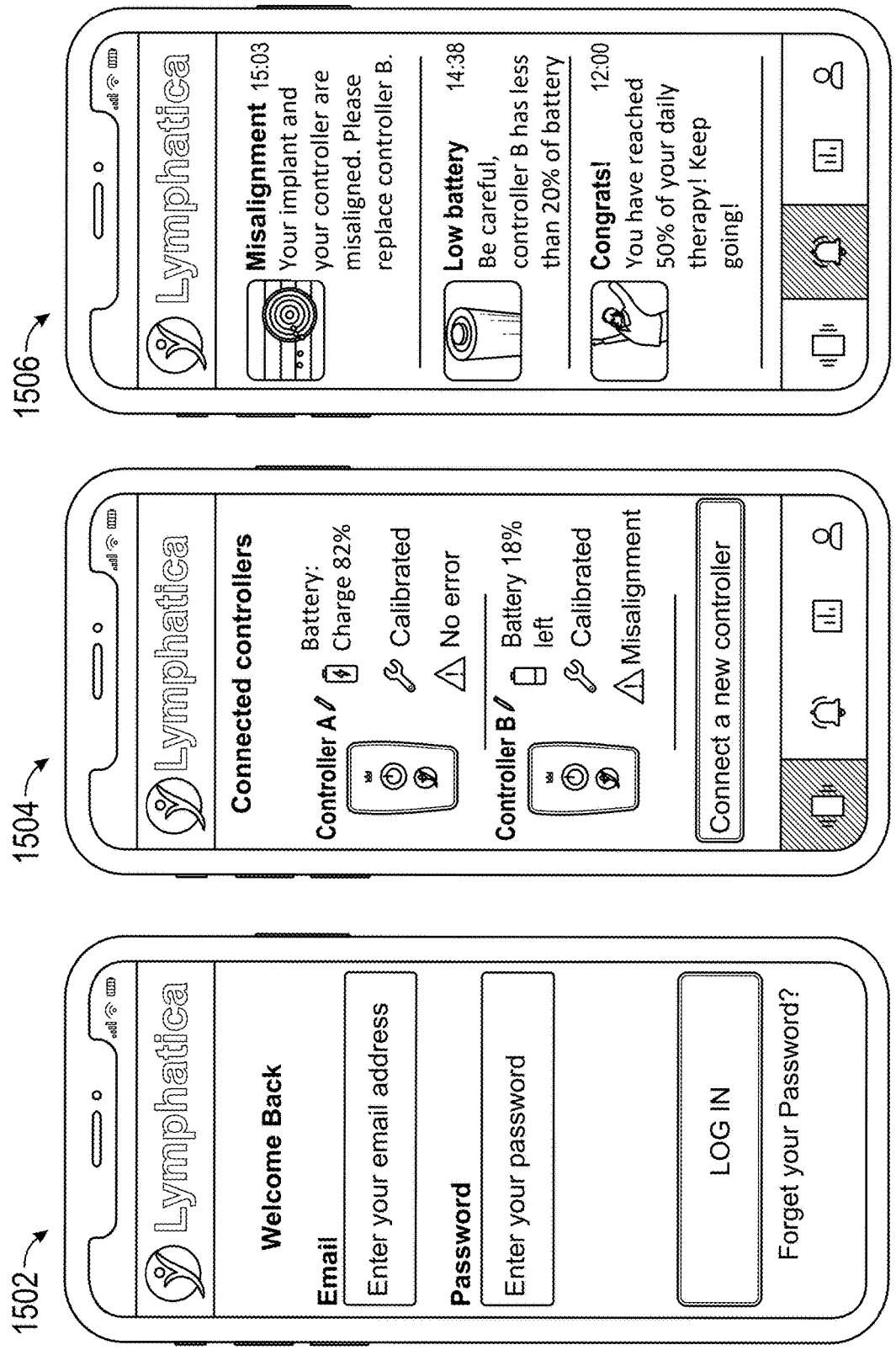
FIG. 15 illustrates exemplary graphic user interfaces to be displayed on a user device and/or health provider device for overseeing operation of the implantable pump.

Referring now to FIG. 15, exemplary graphic user interfaces to be displayed on a user device and/or health provider device for overseeing operation of the implantable pump and of the external controllers are illustrated. Interfaces 1502, 1504 and/or 1506 may be displayed on patient device 120 and/or computing device 120. Interface 1502 depicts an exemplary sign in screen for providing a user name (e.g., email) and password for a user or a health care provider to sign into a platform for managing the bodily fluid management system.

Interface 1504 illustrates an interface for overseeing external controllers connected to an implantable pump. For example, a user may have two external controllers for controlling the implantable pump and the interface 1504 illustrates a battery charge amount, whether or not the external controller has been calibrated (e.g., for a specific user) and/or may indicate any errors (e.g., misalignment). Interface 1504 may further include a button for adding a new controller and a dashboard for accessing a platform for overseeing the bodily fluid drainage system. Interface 1506 illustrates an alert page of the platform showing alert messages such as a misalignment message indicating at a certain time that "your implant and your controller are misaligned."

A low battery alert may be included at a certain time and may state "be careful, controller B has less than 20% battery." The platform may also maintain a log of use by the patient and may oversee the progress of pumping throughout the day and/or may generate messages regarding the user's pumping compliance and/or progress. For example, interface 1506 may include a congratulatory alert indicating that "you have reach 50% of your daily therapy" and "keep going." It is understood that any other alerts or messages may be used.

FIG. 16 is a schematic block diagram of an illustrative external controller 1600 in accordance with one or more example embodiments of the disclosure. External controller 1600 may be the same or similar to external controller 104 of FIG. 1 or any other external controllers of FIGS. 2-15.

In an illustrative configuration, external controller 1600 may include one or more processors (processor(s)) 1602, which may be one or more PCBs, one or more memory devices 1604 (generically referred to herein as memory 1604), one or more of the input/output (I/O) interface(s) 1606, which may be one or more engagement portions or buttons, one or more network interface(s) 1608, one or more transceivers 1612, and one or more antenna(s) 1634. External controller 1600 may further include one or more buses 1618 that functionally couple various components of external controller 1600. External controller 1600 may further include one or more antenna(e) 1634 that may include, without limitation, a cellular antenna for transmitting or receiving signals to/from a cellular network infrastructure, an antenna for transmitting or receiving Wi-Fi signals to/from an access point (AP), a Global Navigation Satellite System (GNSS) antenna for receiving GNSS signals from a GNSS satellite, a Bluetooth antenna for transmitting or receiving Bluetooth signals including BLE signals, a Near Field Communication (NFC) antenna for transmitting or receiving NFC signals, a 900 MHz antenna, and so forth. These various components will be described in more detail hereinafter.

Bus(es) 1618 may include at least one of a system bus, a memory bus, an address bus, or a message bus, and may permit exchange of information (e.g., data (including computer-executable code), signaling, etc.) between various components of the external controller 1600. The bus(es) 1618 may include, without limitation, a memory bus or a memory controller, a peripheral bus, an accelerated graphics port, and so forth. The bus(es) 1618 may be associated with any suitable bus architecture including, without limitation, an Industry Standard Architecture (ISA), a Micro Channel Architecture (MCA), an Enhanced ISA (EISA), a Video Electronics Standards Association (VESA) architecture, an Accelerated Graphics Port (AGP) architecture, a Peripheral Component Interconnects (PCI) architecture, a PCI-Express architecture, a Personal Computer Memory Card International Association (PCMCIA) architecture, a Universal Serial Bus (USB) architecture, and so forth.

The memory 1604 of the external controller 1600 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

In various implementations, memory 1604 may include multiple different types of memory such as various types of static random access memory (SRAM), various types of dynamic random access memory (DRAM), various types of unalterable ROM, and/or writeable variants of ROM such as electrically erasable programmable read-only memory (EEPROM), flash memory, and so forth. Memory 1604 may include main memory as well as various forms of cache memory such as instruction cache(s), data cache(s), translation lookaside buffer(s) (TLBs), and so forth. Further, cache memory such as a data cache may be a multi-level cache organized as a hierarchy of one or more cache levels (L1, L2, etc.).

Data storage 1620 may include removable storage and/or non-removable storage including, but not limited to, magnetic storage, optical disk storage, and/or tape storage. Data storage 1620 may provide non-volatile storage of computer-executable instructions and other data. Memory 1604 and the data storage 1620, removable and/or non-removable, are examples of computer-readable storage media (CRSM) as that term is used herein.

Data storage 1620 may store computer-executable code, instructions, or the like that may be loadable into the memory 1604 and executable by the processor(s) 1602 to cause processor(s) 1602 to perform or initiate various operations. Data storage 1620 may additionally store data that may be copied to memory 1604 for use by the processor(s) 1602 during the execution of the computer-executable instructions. Moreover, output data generated as a result of execution of the computer-executable instructions by the processor(s) 1602 may be stored initially in memory 1604, and may ultimately be copied to data storage 1620 for non-volatile storage.

More specifically, data storage 1620 may store one or more operating systems (O/S) 1622; one or more database management systems (DBMS) 1624; and one or more program module(s), applications, engines, computer-executable code, scripts, or the like such as, for example, one or more implementation module(s) 1626, one or more settings module(s) 1627, one or more communication module(s) 1628, and/or one or more motor module(s) 1629. Some or all of these module(s) may be sub-module(s). Sub or all of these module(s) may be part of the catalog service and some or all of these modules may be part of the system. Any of the components depicted as being stored in data storage 1620 may include any combination of software, firmware, and/or hardware. The software and/or firmware may include computer-executable code, instructions, or the like that may be loaded into the memory 1604 for execution by one or more of the processor(s) 1602. Any of the components depicted as being stored in data storage 1620 may support functionality described in reference to correspondingly named components earlier in this disclosure.

The data storage 1620 may further store various types of data utilized by components of the external controller 1600. Any data stored in the data storage 1620 may be loaded into the memory 1604 for use by the processor(s) 1602 in executing computer-executable code. In addition, any data depicted as being stored in the data storage 1620 may potentially be stored in one or more datastore(s) and may be accessed via the DBMS 1624 and loaded in the memory 1604 for use by the processor(s) 1602 in executing computer-executable code. The datastore(s) may include, but are not limited to, databases (e.g., relational, object-oriented, etc.), file systems, flat files, distributed datastores in which data is stored on more than one node of a computer network, peer-to-peer network datastores, or the like.

Processor(s) 1602 may be configured to access the memory 1604 and execute computer-executable instructions loaded therein. For example, the processor(s) 1602 may be configured to execute computer-executable instructions of the various program module(s), applications, engines, or the like of the external controller 1600 to cause or facilitate various operations to be performed in accordance with one or more embodiments of the disclosure. The processor(s) 1602 may include any suitable processing unit capable of accepting data as input, processing the input data in accordance with stored computer-executable instructions, and generating output data. Processor(s) 1602 may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application Specific Integrated Circuit (ASIC), a Field-Programmable Gate Array (FPGA), a System-on-a-Chip (SoC), an application-specific integrated circuit, a digital signal processor (DSP), and so forth. Further, the processor(s) 1602 may have any suitable microarchitecture design that includes any number of constituent components such as, for example, registers, multiplexers, arithmetic logic units, cache controllers for controlling read/write operations to cache memory, branch predictors, or the like. The microarchitecture design of processor(s) 1602 may be capable of supporting any of a variety of instruction sets.

Referring now to functionality supported by the various program module(s) depicted in FIG. 16, the implementation module(s) 1626 may include computer-executable instructions, code, or the like that responsive to execution by one or more of the processor(s) 1602 may perform functions including, but not limited to, overseeing coordination and interaction between one or more modules and computer executable instructions in data storage 1620. Implementation module 1626 may further coordinate with communication module 1628 to send messages to and receive messages from other devices.

The settings module(s) 1627 may include computer-executable instructions, code, or the like that responsive to execution by one or more of the processor(s) 1602 may perform functions including, but not limited to, determining settings for operating a motor including pump parameters, frequency of operation, and/or any patient parameters or settings.

The communication module(s) 1628 may include computer-executable instructions, code, or the like that responsive to execution by one or more of the processor(s) 1602 may perform functions including, but not limited to, communicating with one or more devices or servers, for example, via wired or wireless communication, communicating with electronic devices, communicating with one or more servers (e.g., remote servers), communicating with remote datastores and/or databases, sending or receiving notifications or commands/directives, communicating with cache memory data, and the like.

The motor module(s) 1629 may include computer-executable instructions, code, or the like that responsive to execution by one or more of the processor(s) 1602 may perform functions including, but not limited to, operating the motor to move the driving magnet based on pump parameters and patient specific parameters or information determined by settings module 1627.

Referring now to other illustrative components of the external controller 1600, the optional input/output (I/O)

interface(s) 1606 may facilitate the receipt of input information by the external controller 1600 from one or more I/O devices as well as the output of information from the external controller 1600 to the one or more I/O devices. The I/O devices may include any of a variety of components such as a button, toggle, or display screen having a touch surface or touchscreen; an audio output device for producing sound, such as a speaker; an audio capture device, such as a microphone; an image and/or video capture device, such as a camera; a haptic unit; and so forth. Any of these components may be integrated into the external controller 1600 or may be separate. The I/O devices may further include, for example, any number of peripheral devices such as data storage devices, printing devices, and so forth.

The antenna(e) 1634 may include any suitable type of antenna depending, for example, on the communications protocols used to transmit or receive signals via the antenna (e) 1634. Non-limiting examples of suitable antennas may include directional antennas, non-directional antennas, dipole antennas, folded dipole antennas, patch antennas, multiple-input multiple-output (MIMO) antennas, or the like. The antenna(e) 1634 may be communicatively coupled to one or more transceivers 1612 or radio components to which or from which signals may be transmitted or received.

As previously described, the antenna(e) 1634 may include a Bluetooth antenna configured to transmit or receive signals in accordance with established standards and protocols, such as Bluetooth and/or BLE. Alternatively, or in addition to, antenna(e) 1634 may include cellular antenna configured to transmit or receive signals in accordance with established standards and protocols, such as or cellular antenna configured to transmit or receive signals in accordance with established standards and protocols, such as Global System for Mobile Communications (GSM), 3G standards (e.g., Universal Mobile Telecommunications System (UMTS), Wideband Code Division Multiple Access (W-CDMA), CDMA2000, etc.), 4G standards (e.g., Long-Term Evolution (LTE), WiMax, etc.), direct satellite communications, or the like. The antenna(e) 1634 may additionally, or alternatively, include a Wi-Fi® antenna configured to transmit or receive signals in accordance with established standards and protocols, such as the IEEE 802.11 family of standards, including via 2.4 GHz channels (e.g., 802.11b, 802.11g, 802.11n), 5 GHz channels (e.g., 802.11n, 802.11ac), or 60 GHz channels (e.g., 802.11ad). In alternative example embodiments, the antenna(e) 1634 may be configured to transmit or receive radio frequency signals within any suitable frequency range forming part of the unlicensed portion of the radio spectrum (e.g., 900 MHz).

The transceiver(s) 1612 may include any suitable radio component(s) for—in cooperation with the antenna(e) 1634—transmitting or receiving radio frequency (RF) signals in the bandwidth and/or channels corresponding to the communications protocols utilized by the external controller 1600 to communicate with other devices. The transceiver(s) 1612 may include hardware, software, and/or firmware for modulating, transmitting, or receiving—potentially in cooperation with any of antenna(e) 1634—communications signals according to any of the communications protocols discussed above including, but not limited to, one or more Wi-Fi® and/or Wi-Fi® direct protocols, as standardized by the IEEE 802.11 standards, one or more non-Wi-Fi® protocols, or one or more cellular communications protocols or standards. The transceiver(s) 1612 may further include hardware, firmware, or software for receiving GNSS signals. The transceiver(s) 1612 may include any known receiver and baseband suitable for communicating via the communications protocols utilized by the external controller 1600. The transceiver(s) 1612 may further include a low noise amplifier (LNA), additional signal amplifiers, an analog-to-digital (A/D) converter, one or more buffers, a digital baseband, or the like.

It should be appreciated that the program module(s), applications, computer-executable instructions, code, or the like depicted in FIG. 16 as being stored in the data storage 1620 are merely illustrative and not exhaustive and that processing described as being supported by any particular module may alternatively be distributed across multiple module(s) or performed by a different module. It should further be appreciated that the external controller 1600 may include alternate and/or additional hardware, software, or firmware components beyond those described or depicted without departing from the scope of the disclosure. More particularly, it should be appreciated that software, firmware, or hardware components depicted as forming part of the external controller 1600 are merely illustrative and that some components may not be present or additional components may be provided in various embodiments. While various illustrative program module(s) have been depicted and described as software module(s) stored in data storage 1620, it should be appreciated that functionality described as being supported by the program module(s) may be enabled by any combination of hardware, software, and/or firmware. It should further be appreciated that each of the above-mentioned module(s) may, in various embodiments, represent a logical partitioning of supported functionality. This logical partitioning is depicted for ease of explanation of the functionality and may not be representative of the structure of software, hardware, and/or firmware for implementing the functionality. Accordingly, it should be appreciated that functionality described as being provided by a particular module may, in various embodiments, be provided at least in part by one or more other module(s). Further, one or more depicted module(s) may not be present in certain embodiments, while in other embodiments, additional module(s) not depicted may be present and may support at least a portion of the described functionality and/or additional functionality. Moreover, while certain module(s) may be depicted and described as sub-module(s) of another module, in certain embodiments, such module(s) may be provided as independent module(s) or as sub-module(s) of other module(s).

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

It should be understood that any of the computer operations described herein above may be implemented at least in part as computer-readable instructions stored on a computer-readable memory. It will of course be understood that the embodiments described herein are illustrative, and components may be arranged, substituted, combined, and designed in a wide variety of different configurations, all of which are contemplated and fall within the scope of this disclosure.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A lymphatic drainage system for lymphatic fluid management in a patient, the lymphatic drainage system comprising an implantable pump comprising:
    a housing configured to be implanted within the patient;
    an inlet tube configured to be in fluid communication with a first bodily portion to receive bodily fluid;
    an outlet tube configured to be in fluid communication with a second bodily portion;
    a fluid chamber disposed within the housing and configured to be in fluid communication with the inlet tube and the outlet tube;
    a rotor disposed within the housing and configured to rotate to change a volume of the fluid chamber; and
    a first membrane defining a wall of the fluid chamber, the first membrane configured to stretch responsive to rotation of the rotor to reduce the volume of the fluid chamber towards a closed position such that the bodily fluid is pumped from the first bodily portion towards the second bodily portion via the inlet tube, the fluid chamber, and the outlet tube,
    wherein the first membrane is configured to be positioned at least partially around the rotor.

2. The lymphatic drainage system of claim 1, further comprising a second membrane defining a second wall of the fluid chamber, wherein the first membrane and the second membrane are hermetically sealed to form the fluid chamber.

3. The lymphatic drainage system of claim 2, wherein the second membrane does not change shape responsive to rotation of the rotor.

4. The lymphatic drainage system of claim 2, further comprising a rigid shell, wherein the second membrane is coupled to the rigid shell and is restrained from moving by the rigid shell.

5. The lymphatic drainage system of claim 2, wherein the fluid chamber is configured to receive the bodily fluid from the inlet tube and wherein the bodily fluid is contained between the first membrane and the second membrane.

6. The lymphatic drainage system of claim 1, further comprising a catheter comprising a first end positioned in the first bodily portion and a second end coupled to the inlet tube.

7. The lymphatic drainage system of claim 6, wherein the catheter comprises a plurality of lumens, each lumen having a different length.

8. The lymphatic drainage system of claim 7, wherein each lumen of the plurality of lumens comprises an opening and each respective opening is axially displaced along the catheter from each other opening of the plurality of lumens.

9. The lymphatic drainage system of claim 7, wherein each lumen of the plurality of lumens comprises an opening and each respective opening is radially displaced along the catheter from each other opening of the plurality of lumens.

10. The lymphatic drainage system of claim 7, wherein each lumen of the plurality of lumens converges into an outlet lumen of the catheter.

11. The lymphatic drainage system of claim 6, wherein the inlet tube, the catheter, the outlet tube, and the first membrane are all made of the same material.

12. The lymphatic drainage system of claim 11, wherein the material comprises a silicone elastomer coated with covalent heparin, and
    wherein the bodily fluid only contacts the material when using the implantable pump.

13. The lymphatic drainage system of claim 1, further comprising a piston configured to interface with the rotor, wherein the rotor causes piston to transition between a first position and a second position.

14. The lymphatic drainage system of claim 13, wherein the piston is configured to interface with the first membrane and wherein the first membrane is caused to stretch as the piston transitions between the first position and the second position.

15. The lymphatic drainage system of claim 1, further comprising a lever in mechanical communication with the rotor and configured to move between an open position and a closed position responsive to rotation of the rotor to cause the inlet tube to periodically kink such that the bodily fluid is pumped from the first bodily portion towards the second bodily portion via the inlet tube, the fluid chamber, and the outlet tube.

16. A method for pumping lymphatic fluid in a patient, the method comprising:
    implanting an implantable pump comprising a housing, an inlet tube, a fluid chamber comprising a first membrane defining a wall of the fluid chamber, an outlet tube, and a rotor;
    causing the rotor to rotate to cause the rotor to transition between an intake position and a discharge position to change a volume of the fluid chamber to cause a bodily from a first bodily portion to move from the inlet tube to the outlet tube;
    wherein the first membrane is configured to stretch responsive to rotor to reduce the volume of the fluid chamber such that bodily fluid is pumped from the first bodily portion via the inlet tube into the fluid chamber and out to a second bodily portion via the outlet tube, the inlet tube in fluid communication with the first bodily portion and the fluid chamber and the outlet tube in fluid communication with the second bodily portion and the fluid chamber, and
    wherein the first membrane is configured to be positioned at least partially around the rotor.

17. The method of claim 16, wherein the implantable pump further comprises a second membrane that defines a second wall of the fluid chamber, wherein the first membrane and the second membrane are hermetically sealed to form the fluid chamber.

18. The method of claim 17, wherein the second membrane does not change shape responsive to rotation of the rotor.

19. The method of claim 17, wherein the implantable pump further comprises a rigid shell and wherein the second membrane is coupled to the rigid shell and is restrained from moving by the rigid shell.

20. The method of claim 16, further comprising causing the rotor to transition from the discharge position to the intake position to change the volume of the fluid chamber to cause bodily fluid from the first bodily portion to move from the inlet tube to the fluid chamber.

21. The method of claim 16, wherein the inlet tube is coupled to a catheter comprising a first end positioned in the first bodily portion and a second end coupled to the inlet tube.

22. The method of claim 21, wherein the catheter comprises a plurality of lumens, each lumen having a different length.

23. The method of claim 22, wherein each lumen of the plurality of lumens comprises an opening and each respective opening is axially displaced along the catheter from each other opening of the plurality of lumens.

24. The method of claim 22, wherein each lumen of the plurality of lumens comprises an opening and each respective opening is radially displaced along the catheter from each other opening of the plurality of lumens.

25. The method of claim 22, wherein each lumen of the plurality of lumens converges into an outlet lumen of the catheter.

26. The method of claim 21, wherein the inlet tube, the catheter, the outlet tube, and the first membrane are all made of the same material.

27. The method of claim 26, wherein the material comprises a silicone elastomer coated with covalent heparin, and wherein the bodily fluid only contacts the material when using the implantable pump.

28. The method of claim 16, wherein the implantable pump further comprises a piston configured to interface with the rotor and the first membrane, and wherein causing the rotor to transition between the intake position and a discharge position causes the piston to transition between a first position and a second position.

29. The method of claim 28, wherein the piston is configured to interface with the first membrane and wherein the membrane is caused to stretch as the piston transitions between the first position and the second position.

30. The method of claim 16, wherein the implantable pump further comprises a lever in mechanical communication with the rotor, wherein the lever is configured to move between an open position and a closed position responsive to rotation of the rotor to cause the inlet tube to periodically kink such that the bodily fluid is pumped from the first bodily portion towards the second bodily portion via the inlet tube, the fluid chamber, and the outlet tube.

* * * * *